(12) United States Patent
McWeeney et al.

(10) Patent No.: US 9,877,708 B2
(45) Date of Patent: Jan. 30, 2018

(54) EXCHANGEABLE CORE BIOPSY NEEDLE

(71) Applicant: COVIDIEN LP, Mansfield, MA (US)

(72) Inventors: John O. McWeeney, Brighton, MA (US); Stephen Tully, Waltham, MA (US); Eugene Campbell, Natick, MA (US); Bora Gumustop, Slingerlands, NY (US); Brian Tinkham, Sciterate, MA (US)

(73) Assignee: COVIDIEN LP, Mansfield, MA (US)

( * ) Notice: Subject to any disclaimer, the term of this patent is extended or adjusted under 35 U.S.C. 154(b) by 262 days.

(21) Appl. No.: 14/755,018

(22) Filed: Jun. 30, 2015

(65) Prior Publication Data

US 2016/0030015 A1 Feb. 4, 2016

Related U.S. Application Data

(60) Provisional application No. 62/030,661, filed on Jul. 30, 2014, provisional application No. 62/030,670, filed on Jul. 30, 2014, provisional application No. 62/030,681, filed on Jul. 30, 2014.

(51) Int. Cl.
*A61B 10/02* (2006.01)
*A61B 8/08* (2006.01)
A61B 10/04 (2006.01)

(52) U.S. Cl.
CPC ........ *A61B 10/0266* (2013.01); *A61B 8/0841* (2013.01); *A61B 10/0233* (2013.01); *A61B 10/0275* (2013.01); *A61B 10/0283* (2013.01); *A61B 2010/0225* (2013.01); *A61B 2010/045* (2013.01)

(58) Field of Classification Search
CPC .................................................. A61B 10/0266
See application file for complete search history.

(56) References Cited

U.S. PATENT DOCUMENTS

| | | | |
|---|---|---|---|
| 4,708,147 | A | 11/1987 | Haaga |
| 4,850,354 | A | 7/1989 | McGurk-Burleson |
| 4,983,179 | A | 1/1991 | Sjostrom |
| 5,615,690 | A | 4/1997 | Giurtino |
| 6,009,933 | A | 1/2000 | Doyle |
| 6,027,514 | A | 2/2000 | Stine |
| 2006/0030785 | A1 | 2/2006 | Field |
| 2009/0018468 | A1 | 1/2009 | Janssens |
| 2011/0224577 | A1 | 9/2011 | Park |

(Continued)

FOREIGN PATENT DOCUMENTS

| | | |
|---|---|---|
| EP | 0221007 A1 | 5/1987 |
| EP | 2520237 A1 | 11/2012 |

(Continued)

OTHER PUBLICATIONS

Chinese Office Action dated Feb. 6, 2016, for CN App. Model No. 201520562976.8, from the Chinese Patent Office.

(Continued)

*Primary Examiner* — Rochelle Turchen

(57) ABSTRACT

The present disclosure provides biopsy needles configured to maximize tissue sampling yield and further ensure collection of a cohesive unit of sampled tissue. The biopsy needles of the present disclosure provide a distinct tissue collection distal end configured to collect a full core of tissue sample and keep the full core intact. The distal end may include a distinct helical slot extending from an open distal end or a distinct cutting tip forming a coring feature.

10 Claims, 18 Drawing Sheets

(56) References Cited

U.S. PATENT DOCUMENTS

| | | |
|---|---|---|
| 2012/0116248 A1 | 5/2012 | McWeeney |
| 2012/0130274 A1 | 5/2012 | Persat |
| 2012/0165832 A1 | 6/2012 | Oostman, Jr. |
| 2012/0253228 A1 | 10/2012 | Schembre |
| 2012/0289985 A1 | 11/2012 | Motai |
| 2013/0102925 A1 | 4/2013 | McGhie |
| 2015/0313580 A1 | 11/2015 | Dejima et al. |

FOREIGN PATENT DOCUMENTS

| | | |
|---|---|---|
| EP | 2982309 A1 | 2/2016 |
| JP | H07100140 A | 4/1995 |
| WO | 9508291 A1 | 3/1995 |
| WO | 9724070 A1 | 7/1997 |
| WO | 2011126963 A2 | 10/2011 |
| WO | 2013074653 A1 | 5/2013 |
| WO | 2014112518 A1 | 7/2014 |

OTHER PUBLICATIONS

EP extended European Search Report for Application No. 15178995.5 dated May 23, 2016, from the European Patent Office.
EP partial European search report for Application No. 15178995.5 dated Feb. 3, 2016, from the European Patent Office.
EP extended European search report for Application No. 15191407.4 dated Jun. 3, 2016 from the European Patent Office.
EP extended European search report for Application No. 15178119.2 dated Jan. 11, 2016 from the European Patent Office.
Notice of Reasons for Rejection for Japanese Patent Application No. 2015-148633, dated Aug. 3, 2016, from the Japanese Patent Office.
Notice of Reasons for Rejection for Japanese Patent Application No. 2015-146692, dated Aug. 3, 2016, from the Japanese Patent Office.

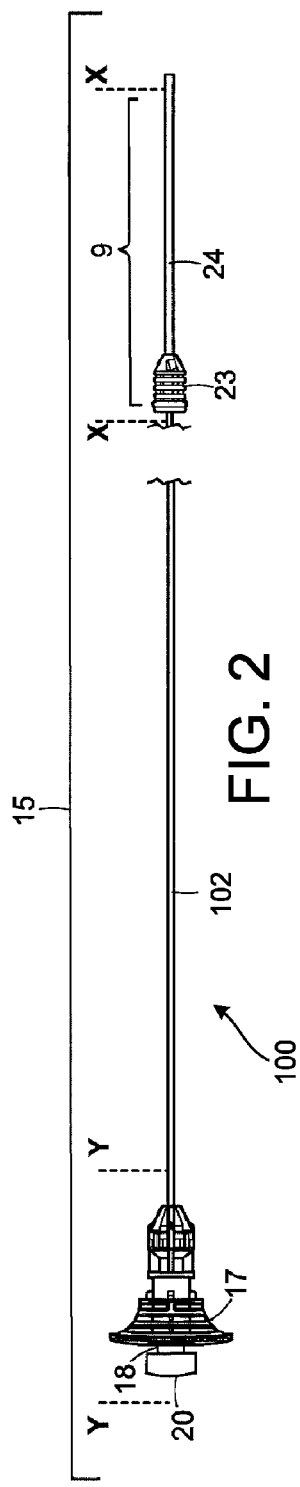
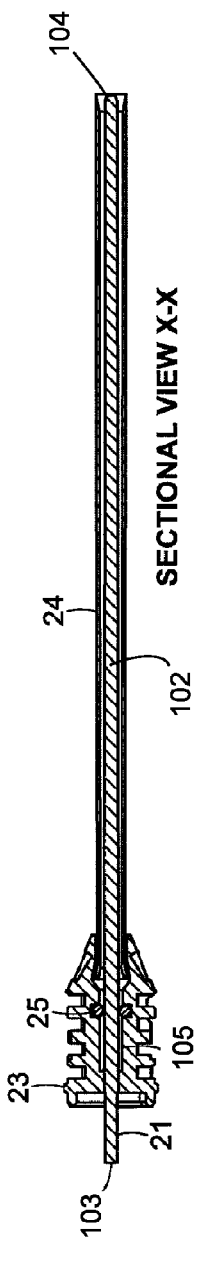
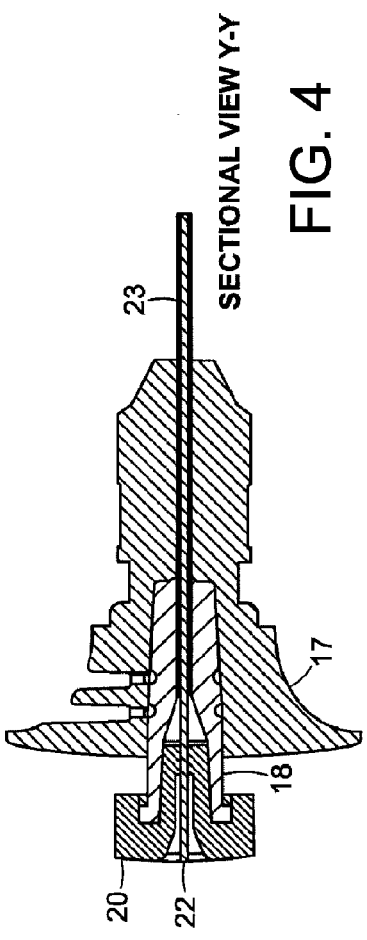
FIG. 2
FIG. 3 SECTIONAL VIEW X-X
FIG. 4 SECTIONAL VIEW Y-Y

EXCHANGEABLE CORE BIOPSY NEEDLE

CROSS REFERENCES TO RELATED APPLICATION

The present application claims the benefit of and priority to U.S. Provisional Application No. 62/030,661, U.S. Provisional Application No. 62/030,670, and U.S. Provisional Application No. 62/030,681, all of which were filed on Jul. 30, 2014. This application is related to U.S. patent application Ser. No. 14/754,966, and U.S. patent application Ser. No. 14/755,140, both of which were filed on Jun. 30, 2015. The entire contents of each of the above applications are incorporated herein by reference.

FIELD OF THE INVENTION

The present disclosure generally relates to biopsy devices, and, more particularly, to a biopsy needle configured for collecting tissue, fluid, and/or cell samples in conjunction with minimally-invasive procedures, such as endoscopic biopsy procedures.

BACKGROUND

In the practice of medical diagnostics, it is often necessary to perform a biopsy to remove a sample of a patient's tissue or fluid for pathological study. For example, biopsies can be useful in diagnosing various forms of cancer and other diseases affecting a localized area of tissue. Biopsy procedures may be used to take tissue and/or fluid samples from muscles, bones and organs, such as the liver or lungs. In some instances, a biopsy sample may be obtained by invasive surgical procedures. However, minimally invasive biopsy procedures are often preferred, such as fine needle aspiration and fine needle biopsy because such procedures are less traumatic to the patient.

Both fine needle aspiration (FNA) and fine needle biopsy (FNB) procedures rely on a needle for collecting the target sample. Biopsy needles are generally classified as being either an end cutting needle or a side cutting needle. An end cutting needle generally includes a hollow cannula having a beveled, circumferentially sharpened, open end at its distal portion. A stylet may be inserted into the hollow shaft of the cannula and extend flush with the open cutting edge of the cannula to close the open end. When the biopsy needle is inserted, the stylet generally functions to puncture the target site (e.g., tissue mass) where the biopsy specimen is to be taken. The stylet is then withdrawn and the cannula further inserted into the tissue mass, wherein the sharpened and beveled leading end is configured to cut tissue and collect the cut tissue into the open distal end of the cannula. A suction device may be applied to a proximal portion of the cannula so as to draw the tissue into the lumen of the cannula.

Generally, the goal of FNA and/or FNB is to acquire sufficient tissue to allow a diagnosis to be made. Currently, different needle configurations are used to collect different sample types (e.g., intact multi-cell samples useful for histology, cells and fragments useful for cytology, etc.). However, many existing biopsy needles are inefficient when collecting samples. For example, with respect to end cutting needles, some current needle tip designs generally result in tearing of target tissue, which may result in a less than ideal core sample and unnecessary trauma to the surrounding tissue, which may cause further complications to the patient (e.g., internal bleeding, bruising, etc.) requiring further treatment. Side cutting needles suffer from the drawback of not effectively drawing a tissue sample of sufficient size into the notch on the cannula. Accordingly, samples extracted by such biopsy needles may not provide sufficient tissue to perform an adequate examination and thus frequently require additional biopsies to be taken. Additionally, such needles suffer from the disadvantage of having to be advanced into the desired tissue site such that the needle may possibly extend beyond the tissue site, thus resulting in the recovery of an inaccurate or non-usable tissue sample, or even resulting in injury to adjacent organs or structures due to such overpenetration.

Additionally, some needles that obtain a full cylinder or "full core" of tissue have difficulty in withdrawing tissue and/or in maintaining the physical state of the tissue so as to provide an accurate assessment of tissue morphology. For example, some needles rely on scoring and/or mashing techniques during tissue collection, which may result in a damaged tissue sample. Depending on the diagnostics, physical characteristics of tissue, such as placement or orientation of cells or tissue, may be as important, or more important, than the chemical or biological characteristics (e.g. presence of malignant cells or by-products).

Furthermore, current needle tip designs may be insufficient for biopsy of certain types of tissue. For example, some lesions are particularly fibrous (e.g., pancreatic lesions) and are difficult to penetrate. Some bevel designs, such as the standard beveled cutting end of needle 100, may initially pierce a portion of the target lesion, but may then deflect off of, or drift, from the target lesion due to the inadequate tip design and/or inability to fully penetrate the lesion, which results in a poor tissue sample, and may even lead to damage to surrounding tissues or vital organs. Additionally, current bevel designs may merely shear off a portion of the target tissue and fail to collect some, or even all, of the sampled tissue within the lumen of the needle due to inadequate tip design.

SUMMARY

The present disclosure provides biopsy needles configured to maximize tissue sampling yield and further ensure collection of a cohesive unit of sampled tissue. The biopsy needles of the present disclosure are able to overcome the drawbacks of current needles by providing a distinct tissue collection distal end configured to collect a full core of tissue sample and keep the full core intact. The distinct distal end may include a distinct side slot, a helical slot extending from an open distal end, or a distal cutting tip forming a coring feature.

In certain aspects, the present disclosure provides a biopsy needle that includes an elongate tubular body having a longitudinal axis. The body includes a proximal portion having a proximal end, a distal portion having a distal end, an outer surface, and an inner surface defining a lumen extending along the longitudinal axis between the proximal and distal portions. The biopsy needle further includes a cutting slot defined on one side of the distal portion of the body and extending through the outer and inner surfaces and into the lumen of the body. The cutting slot includes a proximal cutting end and an opposing distal cutting end. The cutting slot further includes opposing sidewalls defined between the proximal and distal cutting ends and extending along a length of the body and parallel to the longitudinal axis. At least one of the proximal and distal cutting ends defines a concave shape, or notch, having a cutting edge configured to excise a sample material upon contact therewith so as to capture the sample material within the lumen of the body.

By providing a slot with both proximal and distal cutting ends, the biopsy needle allows sample collection by movement of the needle in either proximal or distal directions. For example, the distal cutting end is configured to make contact with and excise a sample material upon movement of the needle body in a proximal direction along the longitudinal axis. Similarly, the proximal cutting end is configured to make contact with and excise a sample material upon movement of the needle body in a distal direction along the longitudinal axis. Furthermore, by providing at least one of the proximal and distal cutting ends with a concave shape (such as a V-shape), the cross-sectional area of the cutting slot is increased, effectively increasing the cutting surface area of the slot and the amount of sample material that can be collected within the slot. By increasing the effective cutting surface area, the biopsy needle of the present disclosure is able to guide tissue into the lumen in a controlled manner and maximize the amount of tissue harvested, particularly upon aspiration.

In another aspect, the present disclosure provides a biopsy needle having an elongate tubular body having a longitudinal axis. The body includes an open proximal end, an open distal end, an outer surface, and an inner surface defining a lumen extending along the longitudinal axis between the proximal and distal ends. The needle further includes a cutting tip defined on the distal end of the body. The cutting tip includes first and second portions formed on opposing sides of the needle body and converging at a pointed end. The first portion of the cutting tip generally includes a coring element formed from a first set of bevel grind. The second portion of the cutting tip includes a side slot formed from a second set of bevel grinds. The coring element defines a cutting edge configured to excise sample material upon rotational movement of the needle body about the longitudinal axis so as to capture and draw the sample material within the lumen of the body.

The cutting tip geometry of this biopsy needle provides a novel way of acquiring targeted tissue, particularly when performing a FNA procedure. For example, while advancing the needle into the targeted site, the needle tip pierces the tissue and, upon rotation of the needle body, the coring element of the cutting tip shears and draws the sample material within the lumen, thereby resulting in collection of a core sample targeted specimen, maximizing the amount of sample harvested as a vacuum is applied.

In another aspect, the present disclosure provides an elongate tubular body having a longitudinal axis. The body includes a proximal portion having an open proximal end, a distal portion having an open distal cutting end, an outer surface, and an inner surface defining a lumen extending along the longitudinal axis between the proximal and distal portions. The needle further includes a cutting slot extending from the open distal end in a direction towards the proximal portion of the body. The cutting slot extends through the outer and inner surfaces and into the lumen of the body. The cutting slot includes opposing sidewalls that extend from a proximal surface of the open distal cutting end and terminate at a base wall. The cutting slot further includes a cutting edge defined on at least one of the opposing sidewalls and base wall. The cutting edge is configured to excise a sample material upon contact therewith so as to capture the sample material within the lumen of the body. In some embodiments, the cutting slot has a helical shape, such that the cutting edge of the cutting slot is configured to contact and excise and draw a sample material into the lumen upon rotational movement of the needle body about the longitudinal axis.

The cutting tip geometry of this biopsy needle provides a novel way of acquiring targeted tissue, particularly when performing a FNA procedure. For example, while advancing the needle into the targeted site, the needle tip pierces the tissue and, upon rotation of the needle body, the helical cutting slot shears the sample material, thereby resulting in collection of a core sample targeted specimen, maximizing the amount of sample harvested as a vacuum is applied.

In another aspect, the present disclosure includes a device for needle biopsy. The device includes an adjustable delivery handle system including a delivery handle, at least a portion of which comprises an inner lumen configured to receive one of a plurality of exchangeable needle subassemblies. The adjustable delivery handle system further includes a sheath coupled to a distal end of the handle and having a lumen in fluid communication with the inner lumen of the delivery handle. The device further includes a needle subassembly removably disposed within the inner lumen of the delivery handle and lumen of the sheath, the needle subassembly including an exchangeable biopsy needle. The exchangeable biopsy needle generally includes an elongate tubular body having a longitudinal axis. The needle body further includes a proximal portion having a proximal end, a distal portion having a distal end, an outer surface, and an inner surface defining a lumen extending along the longitudinal axis between the proximal and distal portions. At least one of the distal portion and distal end is configured to capture a sample material within the lumen of the needle during a biopsy procedure.

In some embodiments, the exchangeable biopsy needle includes a cutting slot defined on at least the distal portion of the needle body, wherein the cutting slot extends through the outer and inner surfaces and into the lumen of the body. In one embodiment, the cutting slot includes a proximal cutting end, an opposing distal cutting end, and opposing sidewalls defined between the proximal and distal cutting ends and extending along a length of the body and parallel to the longitudinal axis. At least one of the proximal and distal cutting ends has a cutting edge configured to excise a sample material upon lateral movement of the needle body along the longitudinal access so as to capture the sample material within the lumen of the body. In another embodiment, the cutting slot generally extends from the distal end of the needle body in a direction towards the proximal portion of the needle body and is formed from opposing sidewalls extending from a proximal surface of the distal end and terminating at a base wall, the cutting slot having a helical shape. At least one of the opposing sidewalls and base wall defines a cutting edge configured to excise a sample material upon contact therewith so as to capture the sample material within the lumen of the body.

In some embodiments, the exchangeable biopsy needle includes a cutting tip defined on the distal end of the needle body. The cutting tip generally includes first and second portions formed on opposing sides of the needle body and converging at a pointed end of the cutting tip, wherein the first portion includes a coring element defining a cutting edge configured to excise sample material upon rotational movement of the needle body about the longitudinal axis so as to capture and draw a core of sample material within the lumen of the needle body.

In some embodiments, the exchangeable biopsy needle further includes a collet surrounding a portion thereof and has a diameter sufficient to prevent the needle from entirely passing through a distal end of the sheath of the adjustable delivery handle system. In some embodiments, the needle subassembly further includes a needle protector subassembly releasably coupled to the collet of the needle. The needle protector subassembly further includes a sheath for encasing at least the distal end of the needle upon withdrawal of the needle from the delivery handle and for preventing inadvertent cutting and/or puncturing. Furthermore, the sheath is moveable along a length of the needle body and configured to be retracted in a proximal direction to expose the distal end of the needle for removal of acquired tissue sample from the lumen of the needle.

BRIEF DESCRIPTION OF THE DRAWINGS

FIG. 2 is a drawing of the needle sub-assembly of the device of FIG. 1.

FIG. 3 is a cross-sectional drawing of the needle protector embodiment of the needle sub-assembly of FIG. 2.

FIG. 4 is a cross-sectional drawing of the proximal end of the biopsy needle sub-assembly of FIG. 2.

DETAILED DESCRIPTION

Figure 1:
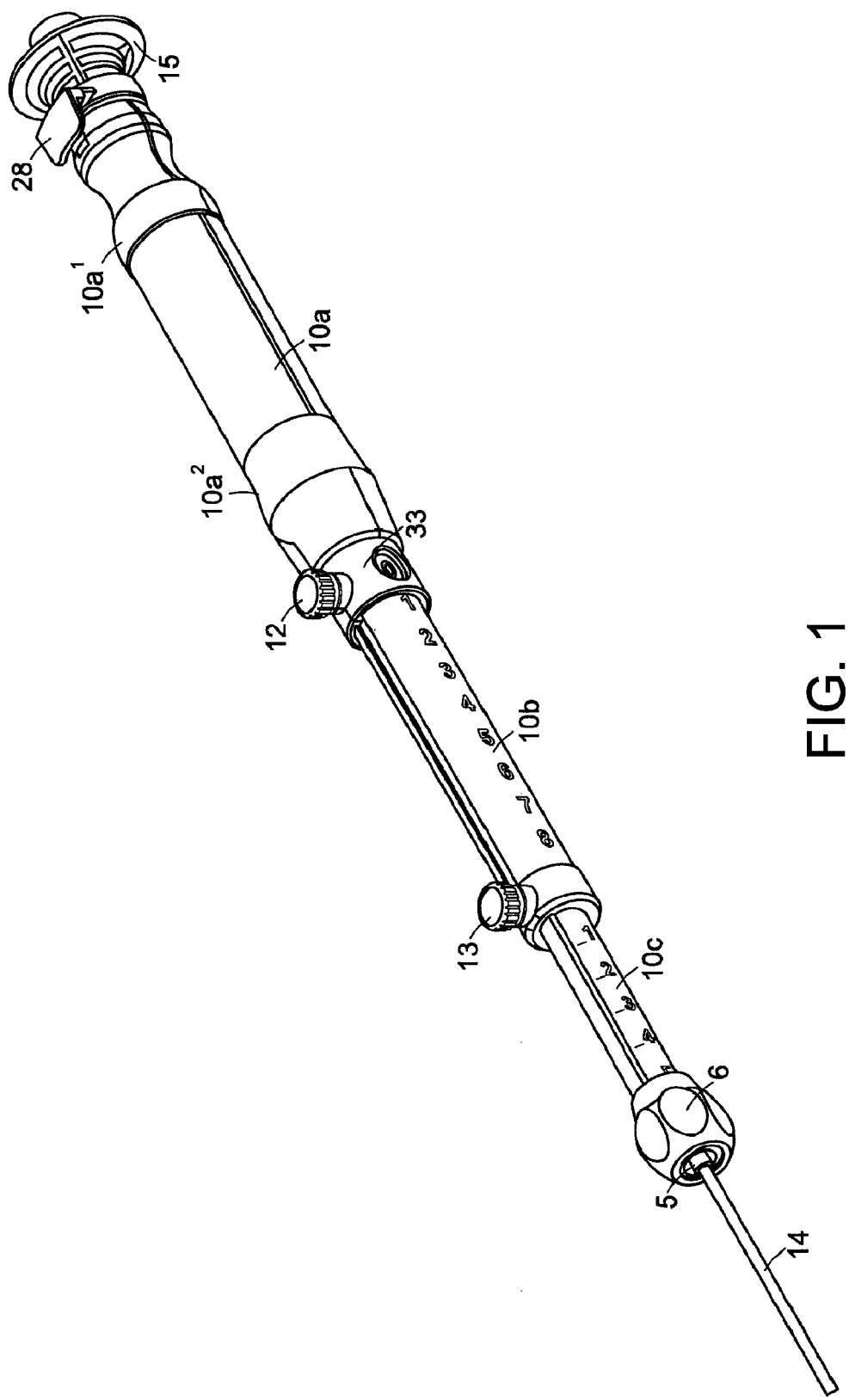
FIG. 1 is a perspective view of a biopsy device including an adjustable delivery handle and sheath for receipt of and use with an exchangeable biopsy needle consistent with the present disclosure.

By way of overview, the present disclosure is generally directed to a biopsy needle configured for collecting tissue, fluid, and/or cell samples in conjunction with minimally-invasive procedures, such as endoscopic biopsy procedures. As described in greater detail herein, a biopsy needle consistent with the present disclosure may be used in Endoscopic Ultrasound (EUS) and Endobronchial Ultrasound (EBUS) procedures, particularly EUS Fine Needle Aspiration (FNA), EUS Fine Needle Biopsy (FNB), EUS Coring, and EBUS procedures for the purpose of harvesting tissue specimen from a targeted site. It should be noted, however, that the biopsy needle may be used in other minimally-invasive procedures, and is not limited to EUS and/or EBUS procedures.

A side cutting needle, sometimes referred to as a TRU-CUT needle, generally includes an inner cannula slidably positioned within an outer cannula. The inner cannula generally has a leveled, circumferentially sharpened distal end shaped to a pointed end with a notch formed at a distal portion of the inner cannula proximate to the pointed end. During a biopsy procedure, the side cutting needle is advanced to the target site (e.g., tissue mass) where the biopsy specimen is to be taken. In some instances, a suction device may be applied to a proximal portion of the inner cannula so as to draw tissue into the notch. At this point, the outer cannula may be advanced over the inner cannula. The outer cannula can have a cutting edge formed about its opening, such that advancement of the cutting edge past the notch of the inner cannula severs the tissue within the notch, thereby encapsulating the tissue sample within. Alternatively, the notch of the inner cannula may include a cutting edge, such that the inner cannula may be rotated or translated in a longitudinal direction so that the cutting edge of the notch severs the tissue specimen. The outer cannula may then be advanced over the inner cannula so as to encapsulate the specimen there between.

In one aspect, the present disclosure provides a biopsy needle that generally includes an elongate tubular body having a longitudinal axis. The body includes a proximal portion having a proximal end, a distal portion having a distal end, an outer surface, and an inner surface defining a lumen extending along the longitudinal axis between the proximal and distal portions. The biopsy needle further includes a cutting slot defined on one side of the distal portion of the body and extending through the outer and inner surfaces and into the lumen of the body. The cutting slot includes a proximal cutting end and an opposing distal cutting end. The cutting slot further includes opposing sidewalls defined between the proximal and distal cutting ends and extending along a length of the body and parallel to the longitudinal axis. At least one of the proximal and distal cutting ends defines a concave shape, or notch, having a cutting edge configured to excise a sample material upon contact therewith so as to capture the sample material within the lumen of the body.

By providing a slot with both proximal and distal cutting ends, the biopsy needle allows sample collection by movement of the needle in either proximal or distal directions. For example, the distal cutting end is configured to make contact with and excise a sample material upon movement of the needle body in a proximal direction along the longitudinal axis. Similarly, the proximal cutting end is configured to make contact with and excise a sample material upon movement of the needle body in a distal direction along the longitudinal axis. During this process, the tissue is excised by the cutting edge, creating a contiguous core biopsy sample.

Furthermore, by providing at least one of the proximal and distal cutting ends with a concave shape (such as a V-shape), the cross-sectional area of the cutting slot is increased when compared to conventional side-cutting needles, effectively increasing the cutting surface area of the slot and the amount of sample material that can be collected within the slot. By increasing the effective cutting surface area, the biopsy needle of the present disclosure is able to guide tissue into the lumen in a controlled manner and maximize the amount of tissue harvested, particularly upon aspiration.

In another aspect, the present disclosure provides a biopsy needle having an elongate tubular body having a longitudinal axis. The body includes an open proximal end, an open distal end, an outer surface, and an inner surface defining a lumen extending along the longitudinal axis between the proximal and distal ends. The needle further includes a cutting tip defined on the distal end of the body. The cutting tip includes first and second portions formed on opposing sides of the needle body and converging at a pointed end. The first portion of the cutting tip includes a side slot formed from a first set of bevel grinds and the second portion of the cutting tip includes a coring element formed from a second set of bevel grinds. The coring element defines a cutting edge configured to excise sample material upon rotational movement of the needle body about the longitudinal axis so as to capture and draw the sample material within the lumen of the body. During this process the tissue is excised by the cutting edge, creating a contiguous core biopsy sample.

The cutting tip geometry of this biopsy needle provides a novel way of acquiring targeted tissue, particularly when performing a FNA procedure. For example, while advancing the needle into the targeted site, the needle tip pierces the tissue and, upon rotation of the needle body, the coring element of the cutting tip shears the sample material, thereby resulting in collection of a core sample targeted specimen, maximizing the amount of sample harvested as a vacuum is applied.

In another aspect, the present disclosure provides an elongate tubular body having a longitudinal axis. The body includes a proximal portion having an open proximal end, a distal portion having an open distal cutting end, an outer surface, and an inner surface defining a lumen extending along the longitudinal axis between the proximal and distal portions. The needle further includes a cutting slot extending from the open distal end in a direction towards the proximal portion of the body. The cutting slot extends through the outer and inner surfaces and into the lumen of the body. The cutting slot includes opposing sidewalls that extend from a proximal surface of the open distal cutting end and terminate at a base wall. The cutting slot further includes a cutting edge defined on at least one of the opposing sidewalls and base wall. The cutting edge is configured to excise a sample material upon contact therewith so as to capture the sample material within the lumen of the body. In some embodiments, the cutting slot has a helical shape, such that the cutting edge of the cutting slot is configured to contact and excise and draw a sample material into the lumen upon rotational movement of the needle body about the longitudinal axis. During this process the tissue is excised by the cutting edge, creating a contiguous core biopsy sample The cutting tip geometry of this biopsy needle provides a novel way of acquiring targeted tissue, particularly when performing a FNA procedure. For example, while advancing the needle into the targeted site, the needle tip pierces the tissue and, upon rotation of the needle body, the helical cutting slot shears the sample material, thereby resulting in collection of a core sample targeted specimen, maximizing the amount of sample harvested as a vacuum is applied.

The distinct sample collecting distal ends of biopsy needles consistent with the present disclosure are configured to collect a full core of tissue sample while keeping the full core intact. Accordingly, biopsy needles consistent with the present disclosure are configured to maximize tissue sampling yield and further ensure collection of a cohesive unit of sampled tissue so as to provide a more complete sample for testing, which may improve the accuracy and/or timing of diagnosis.

The biopsy needle of the present disclosure may be used in conjunction with minimally-invasive procedures, such as endoscopic biopsy procedures. For example, the biopsy needle may be compatible with an endoscopic biopsy device, such as needle biopsy delivery device configured for endoscopic ultrasound or endoscopic bronchial ultrasound procedures. For example, the biopsy needle may be compatible for use with exemplary endoscopic deliver systems and methods discussed in Needle Biopsy Device with Exchangeable Needle and Integrated Needle Protection, U.S. Pub. 2012/0116248, Rapid Exchange FNA Biopsy Device with Diagnostic and Therapeutic Capabilities, U.S. Pub. 2011/0190662, Device for Needle Biopsy with Integrated Needle Protection, U.S. Pub. 2010/0121218, and Needle Biopsy Device, U.S. Pub. 2010/0081965, the contents of each of which are hereby incorporated by reference in their entirety.

An exemplary embodiment of an endoscopic delivery device for use with a biopsy needle of the present disclosure is illustrated in FIG. 1. The device and specific delivery methods are discussed in more detail in Needle Biopsy Device with Exchangeable Needle and Integrated Needle Protection, U.S. Pub. 2012/0116248, the contents of which are hereby incorporated by reference in their entirety. The device design consists of a handle mechanism (delivery system handle 10) and removable needle sub-assembly 15. The delivery system handle 10 includes a proximal handle member 10a, a middle handle member 10b, and a distal handle member 10c. The proximal, middle and distal handle members each include an inner lumen and are coupled together to define a longitudinal axis such that the inner lumens are in constant communication and extends throughout the length of the coupled handle members. Proximal handle member 10a is slideably disposed over at least a portion of the middle handle member 10b, and middle handle member 10b is slideably disposed over at least a portion of distal handle member 10c. The proximal handle member 10a includes proximal handle grip 10a1 a distal handle grip 10a2. The delivery handle system 10 further includes an inner handle member 10d disposed within the inner lumen of the middle handle member 10b.

The delivery system handle 10 also incorporates a sheath 14 component coupled to the distal end of the distal handle member 10c. This component provides a conduit between the delivery system handle 10 and the target sampling site during the exchange of needles, such as the biopsy needle previously described herein. The device design is modular in that the needle sub-assembly 15 can be detached from the proximal handle 10a of the device for each individual "pass" or aspirated sample taken by the endoscopist at the site of the lesion or abnormality.

The delivery system handle 10 incorporates two length adjustment features actuated via adjustment of two thumbscrew locking mechanisms. A threaded proximal thumbscrew 12 and locking ring 33 are moveably disposed around the middle handle member 10b, the proximal thumbscrew 12 is loosened to loosen locking ring 33, locking ring 33 is moved distally along the middle handle member 10b and tightened in the desired position along middle handle member 10b via proximal thumbscrew 12 to allow the user to establish a set depth of needle penetration beyond the end of the sheath 14. A threaded distal thumbscrew 13 is transversely disposed at the distal portion of the middle handle member 10b, the distal thumbscrew 13 is loosened to move the middle handle member 10b distally and/or proximally and tightened to allow the user to establish a set depth of sheath 14 extension beyond the end of the endoscope accessory channel.

The needle sub-assembly 15 consists of at least a biopsy needle consistent with the present disclosure (e.g., needle 100). The body 102 of needle 100 can range in length from 200 mm up to 2500 mm. In some embodiments, the needle body 102 can range in length between 500 mm to 2000 mm. In some embodiments, the needle body 102 can range in length between 800 mm to 1800 mm. In some embodiments, the needle body 102 can range in length between 1640 mm to 1680 mm. The needle sub-assembly 15 further includes needle hub 17, needle luer 18, needle collet 105, needle protector sub-assembly 9, stylet hub 20, and stylet shaft 22.

As generally understood, the needle 100 itself can be manufactured from a variety of metallic based materials, including, but not limited to, nitinol, cobalt chrome, stainless steel, a metal alloy, combinations thereof, nanotube composites, including materials such as carbon, silicon, boron nitride, inorganic materials, or combinations thereof, or polymeric based materials including, but not limited to poly-ether-ether ketone, polyamide, poyethersulfone, polyurethane, ether block amide copolymers, polyacetal, polytetrafluoroethylene and/or derivatives thereof. It should be noted that the biopsy needle is not limited to any particular gauge (e.g., outer diameter). For example, depending on the type of sample to be collected, as well as the target site from which the sample is to be collected, the biopsy needle may range from 10-gauge to 30-gauge, and more specifically 15-gauge to 28-gauge, i.e., gauge 12, 14, 15, 16, 17, 18, 19, 20, 21, 22, 23, 24, or 25 needles.

FIG. 2 is a drawing of the needle sub-assembly 15 of the device of FIG. 1. The sub-assembly 15 is inserted into and removed from the lumen of the delivery system handle 10 in acquiring tissue samples. The sub-assembly 15 consists of stylet hub 20 and stylet shaft 22 components which are securely locked on the needle luer 18 of the needle 100 via conventional internal luer threads, as generally understood by one skilled in the art. The stylet hub 20 may be attached to the stylet shaft 22 via any known processing techniques, including, but not limited to, adhesive bonding or insert injection molding. The female luer of the needle 100 incorporates a mating luer thread detail, onto which the stylet hub 20 may be tightened. The needle luer 18 element of the present disclosure may be attached to the proximal end of the needle shaft via a number of processing techniques such as adhesive bonding or insert injection molding.

The removable needle sub-assembly 15 also incorporates a needle collet 105. The function of this needle collet 105 is to provide a means to center the needle body 102 in the sheath 14 of the delivery system during needle exchange and provide a mechanism for securing and locking the needle protector sub-assembly to the distal end 104 needle 100 once the needle 100 has been unlocked and withdrawn from the delivery system handle. The needle collet 105 of the present disclosure may be attached to a portion of the needle body 102 near the distal end 104 of the needle 100 by way of any known processing techniques, including, but not limited to, adhesive bonding, laser welding, resistance welding, insert injection molding, and combinations thereof. The needle collet 105 may be fabricated from metals materials such as stainless steel, nickel titanium or alloys thereof or polymer materials such as, but not limited to, polyacetal, polyamide, poly-ether-block-amide, polystyrene, acrylonitrile butadiene styrene or derivatives thereof.

FIG. 3 illustrates the needle protection sub-assembly 9 design embodiment of the present disclosure in the locked position at the distal end 104 of the needle 100. The needle protection sub-assembly 9 consists of two needle protector (NP) hub halves (collectively 23), which are adhesively bonded to each other, on the proximal end of the needle protector (NP) sheath component 24. Alternatively, the NP hub halves 23 may be snap fit together or may be insert injection molded over the NP sheath 24 to provide a secure bond/attachment between these components in the assembly. The needle protection sub-assembly 9 also incorporates a needle protector (NP) hub O-Ring component 25. The O-Ring component resides in a recessed cut-out in the center of the assembled NP hub halves 23. The NP hub O-Ring 25, in conjunction with the needle collet 105, which is securely attached to a portion of the needle body 102 near the distal end 104 of the needle 100, provides a mechanism for locking the NP sub-assembly 9 onto the end of the needle 100. In this way, the distal end 104, including the pointed tip (described in greater detail herein), is protected, covered and shielded once the needle has been removed from the delivery system handle.

For example, upon acquiring a sample from a target site, the needle 100 may be removed so as to gain access to the sampled material for testing and diagnostic procedures. The needle 100 may be continually withdrawn from the delivery system handle 10, such that the needle collet 105 contacts the NP hub O-ring 25 and further pulls the NP sub-assembly 9 from engagement with needle hub 17, such that the needle 100 is completely removed from the delivery system handle 10 and the NP sheath 24 encases the distal end 104 of the needle 100 to prevent inadvertent "needle sticking". Further, an operator may then pull back the NP sub-assembly 9 from the distal end 104 of the needle 100 so as to collect the sampled material stored within the lumen of the needle 100.

Accordingly, the NP sub-assembly 9 is configured to translate along a length of the needle 100 so as to allow access to the distal end 104 of the needle 100 post acquisition and when the needle 100 is entirely removed from the delivery system handle 10.

FIG. 4 illustrates the needle hub 17 embodiment of the needle sub-assembly. The needle hub 17 provides a mechanism configured to lock the removable needle sub-assembly 15 into the delivery system handle 10 by means of the hub housing 27 and thumb latch 28 components and provides a means to lock the needle protection sub-assembly 9, shown in FIG. 3, into the delivery system device handle 10. As shown, the needle hub component 17 is securely attached to the needle luer 18 and needle body 102. The needle hub element 17 of the present disclosure may be attached to the distal end of the needle luer component 18 via a number of processing techniques such as adhesive bonding or insert injection molding.

In some embodiments, manipulation of the needle hub 17 may cause rotation at the distal end 104 of the needle 100. As described in greater detail herein, the distal end of biopsy needles consistent with the present disclosure may have a distinct cutting configuration configured to excise and biopsy a sample material upon rotational movement. Accordingly, upon rotation of the needle hub 17, the distal end of the needle rotates, resulting in collection of a sample material. In some embodiments, the needle hub 17 may be disengaged from the handle 10 by depressing the thumb latch 28 and detached from the proximal handle 10a member so as to allow an operator to rotate the needle hub 17 to cause rotation of the distal end of the needle for sample collection. In other embodiments, the needle hub 17 may be configured to rotate while remaining coupled to the handle 10. In some embodiments, the needle hub 17 and/or handle 10 may include a mechanism for providing an operator with control over the rotational movement of the needle hub 17 and, in turn, the distal end of the needle. The needle hub 17 and/or handle 10 may further include a feature configured to indicate gradation of rotational movement. For example, in one embodiment, the needle hub 17 and/or handle 10 may include a feature configured to allow the operator to rotate the needle hub 17 in distinct intervals and further provide an audible indication of needle rotation at specific intervals (e.g., provide a clicking sound every ⅛, ¼, ½, etc. of a rotation about a longitudinal axis of the needle body), thereby providing the operator improved control when performing the biopsy procedure. For example, a customizable dial element may be provided which may be configured to limit rotation of the needle hub 17 to a desired setting. Other elements may be included for controlling rotation the needle hub 17, as generally understood by one skilled in the art.

In some instances, it may be preferable to switch needles during a procedure, while still maintaining access to the target site. The delivery system of FIG. 1 is configured to allow rapid needle exchanges without requiring the delivery system to be removed from the scope, as described in greater detail in U.S. Pub. 2012/0116248, the contents of which are hereby incorporated by reference in their entirety. The rapid needle exchange capabilities provided by the delivery system of the present disclosure may further decrease the amount of time required for a biopsy procedure, which may cut down the amount of anesthesia required during a particular procedure, improving patient safety. Additionally, a new biopsy device is not required for each needle, as may be the case with current biopsy devices and techniques. Accordingly, the delivery system and exchangeable needles of the present disclosure can cut down on costs and by preventing unnecessary waste.

It should be noted that any one of the embodiments of biopsy needles consistent with the present disclosure can be used with the delivery system of FIG. 1 and need not be limited to biopsy needle 100.

Figure 5:
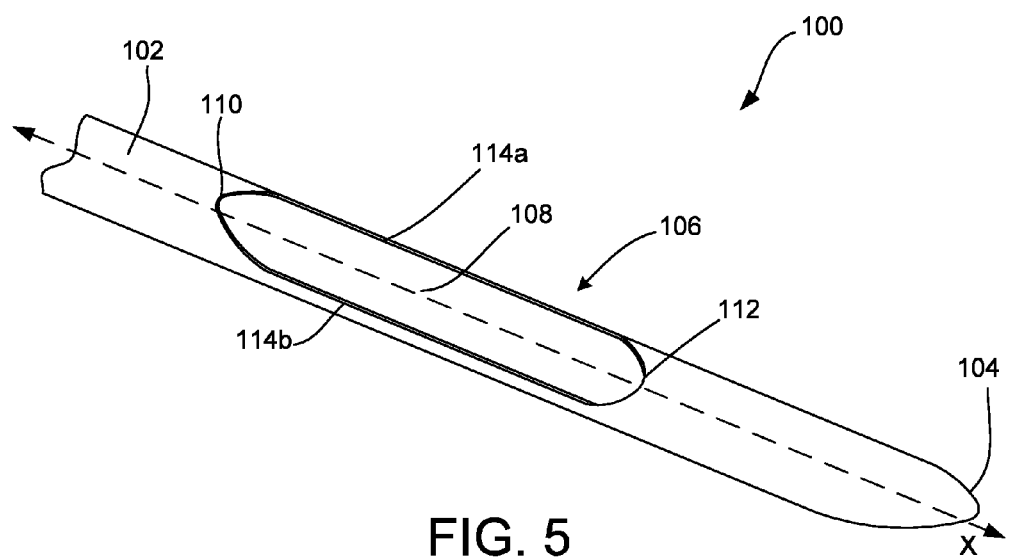
FIG. 5 is a perspective view of a distal portion of biopsy needle consistent with the present disclosure.
Figure 6:
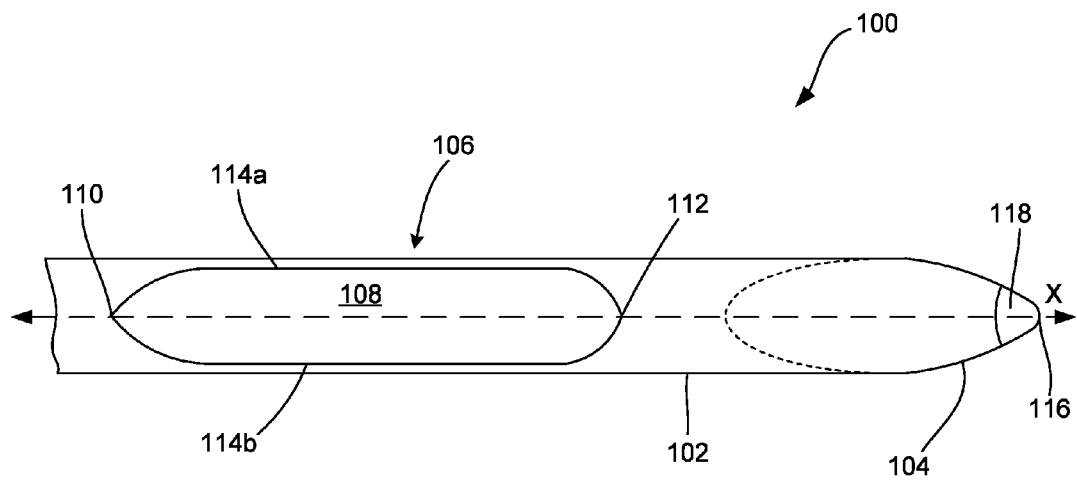
FIG. 6 is a bottom view of the distal portion of the biopsy needle of FIG. 5.
Figure 7:
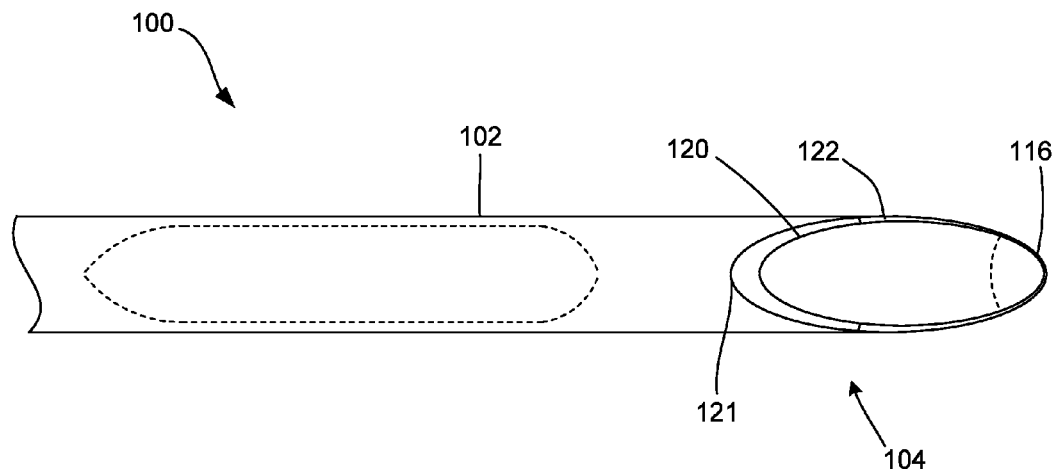
FIG. 7 is a top view of the distal portion of the biopsy needle of FIG. 5.
Figure 8:
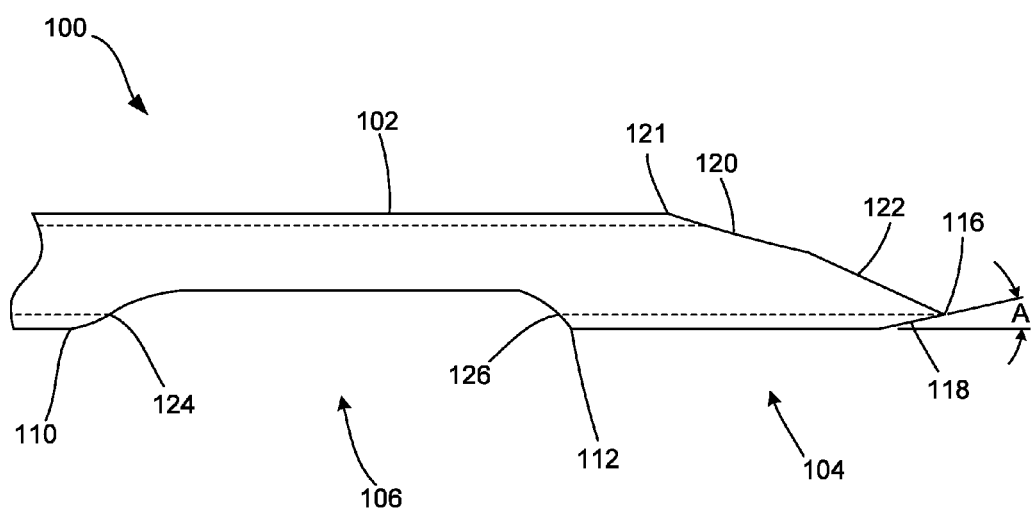
FIG. 8 is a side profile view of the distal portion of the biopsy needle of FIG. 5.

FIGS. 5-8 depict one embodiment of a biopsy needle 100 consistent with the present disclosure. FIG. 5 is a perspective view of a distal portion of biopsy needle 100 consistent with the present disclosure. FIGS. 6-8 are bottom, top, and side profile views of the distal portion of the biopsy needle of FIG. 5. As shown, the needle 200 generally includes an elongate tubular body 102 having a longitudinal axis X. The body 102 includes a proximal portion having a proximal end 103 (shown in FIG. 3), a distal portion having a distal end 104, an outer surface, and an inner surface defining a lumen 108 extending along the longitudinal axis X between the proximal and distal portions. The needle 100 further includes a cutting slot 106 defined on one side of the distal portion of the body 102. The cutting slot 106 generally extends through the outer and inner surfaces and into the lumen 108 of the body 102. As described in greater detail herein, the cutting slot 106 is configured for collection and harvesting of a sample material, including, but not limited to, tissue, fluid, and/or cell samples. In particular, the cutting slot has a distinct shape so as to enhance the ability of the needle 100 to collect tissue during sample acquisition.

As shown, the cutting slot 106 includes a proximal cutting end 110 and an opposing distal cutting end 112 and opposing sidewalls 114a, 144b defined between the proximal and distal cutting ends 110, 112. The opposing sidewalls 114a, 114b generally extend along a length of the body 102 and are parallel to the longitudinal axis X. At least one of the proximal and distal cutting ends 110, 112 and the opposing sidewalls 114a, 114b includes a cutting edge for excising sample material (e.g., tissue) upon contact therewith during biopsy procedure. For example, as shown in FIG. 8, at least the proximal and distal cutting ends 110, 112 each define a cutting edge 124, 126, respectively, such that lateral movement of the needle 100 along the longitudinal axis X in both proximal and distal directions may result in the excision of tissue during a biopsy material (shown in FIGS. 15 and 16).

In some embodiments, the distal end 104 of the needle body 102 may be open, such that the proximal and distal ends 103, 104 are in fluid communication with one another via the lumen 108. It should be noted, however, that in some embodiments, the distal end 104 is closed. In the illustrated embodiment, the open distal end 104 is formed from a set of distinct angular bevel grinds oblique to the outer surface of the body 102. The set of angular bevel grinds may include a first bevel grind 120 extending from a proximal surface 121 of the distal end 104 and towards a pointed tip 116, a second bevel grind 122 extending from the first bevel grind 120 and terminating at the pointed tip 116, and a back-cut bevel grind 118 oblique to first and second bevel grinds 120, 122 and the outer surface of the body 102 and proximate to the pointed tip 116 for providing a smooth needle passage during needle insertion and withdrawal during a biopsy procedure. For example, back-cut grind 118 has a back-cut angle A in the range of 15 degrees to 70 degrees relative to the outer surface of the body 102, but more preferably in the range of 25 degrees to 45 degrees. In one embodiment, the back cut angle A is 30 degrees.

The pointed tip 116 formed from second bevel grind 122 and the back-cut grind 118 may be configured to make contact with and pierce a sample material during a biopsy procedure so as to gain access to a target site and/or excise a sample material, particularly with the aid of aspiration.

The inclusion of at least back-cut grind 118 on the distal end 104 may ensure the smooth passage of the needle down a sheath, or other enclosure of a delivery device, during needle movement and/or exchange. For example, as previously described, the biopsy needle 100 of the present disclosure may be used in conjunction with a delivery device, such as the delivery system of FIG. 1. The endoscopic device may generally include a sheath, or other enclosure, to provide the needle 100 with access to a target site for tissue collection. As such, during a needle exchange, for example, it is important that the needle 100 can be passed through an internal diameter of a sheath of the delivery device without catching on an internal wall of same. As the needle advances, the heel of the back-cut grind 118 may come in contact with the internal diameter of the sheath and reduce the friction between the distal end 104 of the needle 100, particularly the pointed tip 116 and the sheath. In this way, the needle 100 can be smoothly tracked through the sheath to exit the end of the sheath. This feature also makes it easy to remove a needle and re-insert a new needle while the rest of a delivery device remains within a patient during a procedure.

Figure 9:
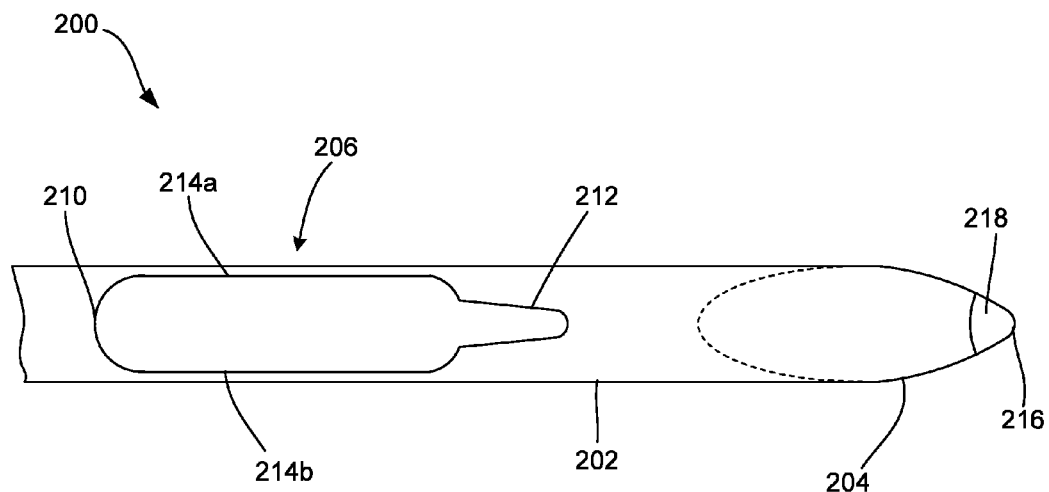
FIG. 9 is a bottom view of a distal portion of another embodiment of a biopsy needle consistent with the present disclosure.
Figure 10:
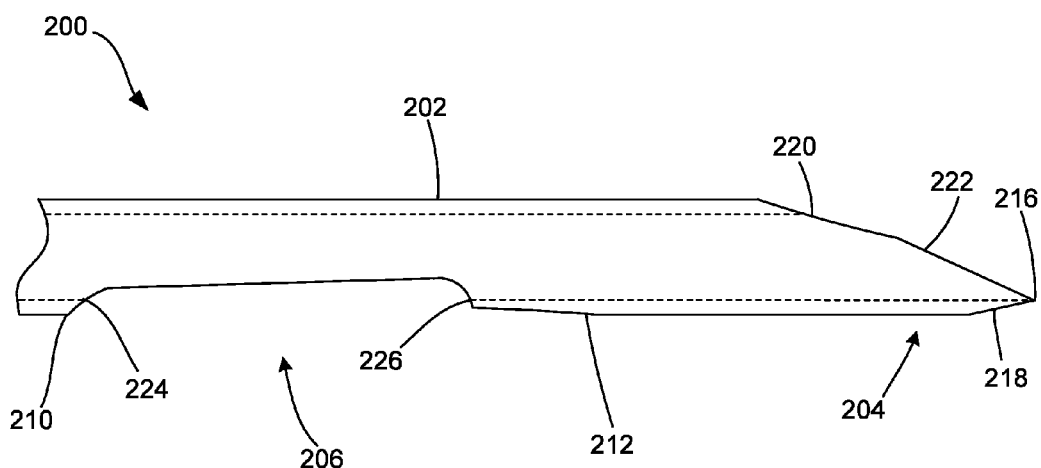
FIG. 10 is a side profile view of a distal portion of another embodiment of a biopsy needle consistent with the present disclosure.

Alternative embodiments of biopsy needles 200, 300 are generally illustrated in FIGS. 9-12. For example, FIGS. 9 and 10 are bottom and side profile views of biopsy needle 200 having an alternative embodiment of a cutting slot 206. In the illustrated embodiment, the distal cutting end 210 of the cutting slot 206 defines a concave shape, generally in a V-shape or a notch. Accordingly, the cutting edge 226 of the distal cutting end 212 has an acute cutting angle. The particular concave shape generally results in an increase in the cross-sectional area of the cutting slot 206, particularly when compared to conventional side-cutting needles, effectively increasing the cutting surface area of the slot 206 and the amount of sample material that can be collected within the slot 206.

Figure 11:
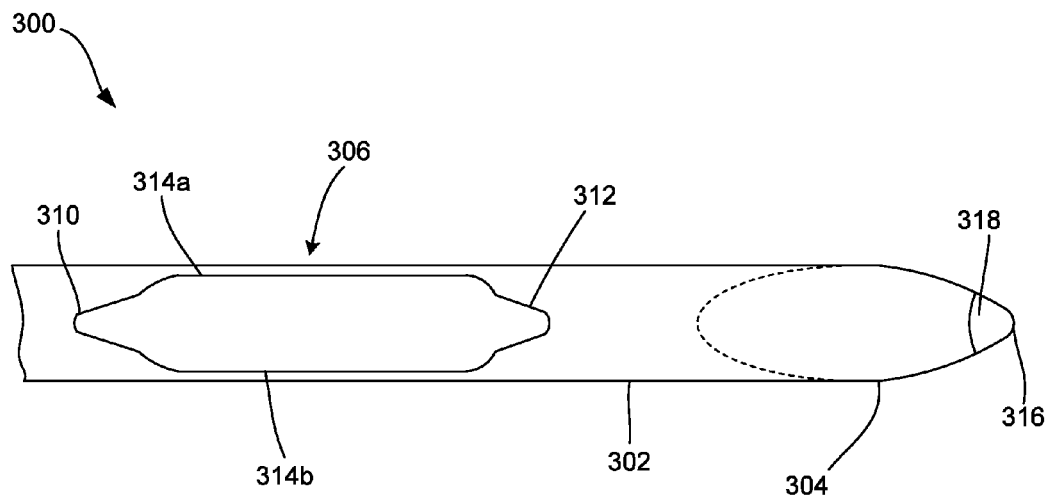
FIG. 11 is a bottom view of a distal portion of another embodiment of a biopsy needle consistent with the present disclosure.
Figure 12:
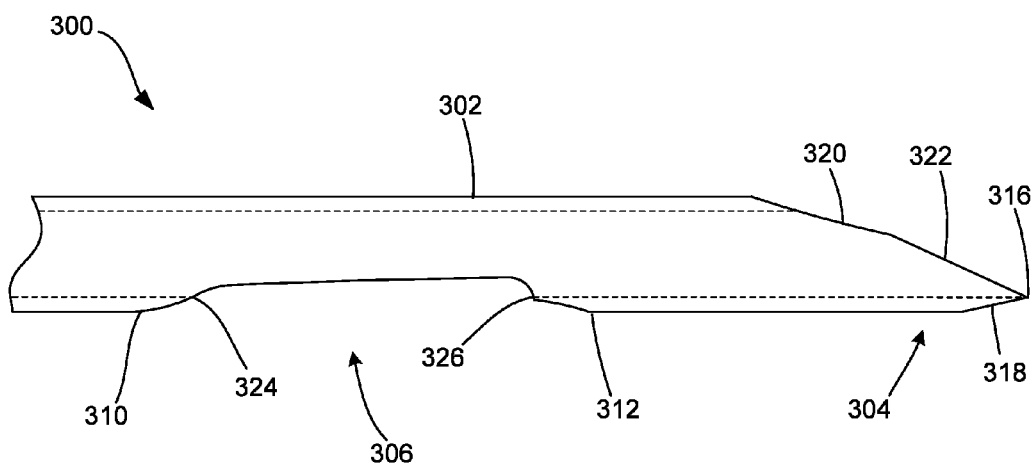
FIG. 12 is a side profile view of a distal portion of another embodiment of a biopsy needle consistent with the present disclosure.

FIGS. 11 and 12 are bottom and side profile views of biopsy needle 300 having an alternative embodiment of a cutting slot 306. In this embodiment, both the proximal and distal cutting ends 310, 312 of the cutting slot 306 have a concave shape, generally in a V-shape or notch. As such, the cross-sectional area of the cutting slot 306 of needle 300 is further increased, effectively increasing the cutting surface area of the slot 306 and the amount of sample material that can be collected within the slot 306.

Figure 13:
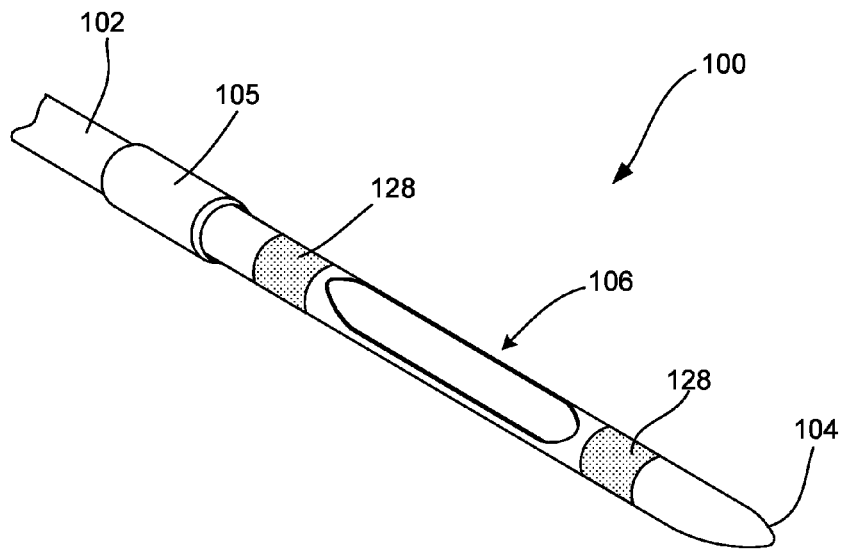
FIG. 13 is a perspective view of the biopsy needle of FIG. 5 including a collet consistent with the present disclosure.

FIG. 13 is a perspective view of a portion of the biopsy needle 100 near the distal end. As shown, the needle 100 further includes collet 105 coupled to a portion of the needle body 102. The length of the needle collet 105 may be in the range of 2 mm to 10 mm, but more preferably in the range of 3.5 mm to 5 mm. It is preferable that the outer diameter of the needle collet 105 be in the range of 0.030 inches to 0.080 inches, but more preferably in the range of 0.040 inches to 0.070 inches, depending on the gauge of the needle 100. The needle collet component 105 may be chamfered at the proximal and distal ends thereof. In some embodiments, it may be preferable that the chamfer angle of the needle collet 105 be in the range of 15 degrees to 80 degrees, relative to a longitudinal axis X of the needle 100, but more preferably in the range of 30 degrees to 60 degrees. The chamfer on both ends of the needle collet 105 may provide smooth locking and unlocking with the needle protector sub-assembly 9 during needle exchanges.

The needle collet 105 is located at a set point distance from the distal end 104 of the needle 100. The distance from the distal end 104 of the needle to the proximal collet position on the needle 100 may be within the range of 6 cm to 12 cm, but is more preferably in the range of 7 cm to 9 cm, and more preferably is located 8 cm from the end of the needle 100. This ensures that when the needle is extended to a maximum extension distance relative to the distal end 14a of the sheath (i.e. 8 cm), the collet 105 does not exit the end of sheath 14, as shown in FIGS. 14A and 14B.

In the illustrated embodiment, a portion 128 of the needle body 102 adjacent the distal end 104 and/or the cutting slot 106 may incorporate an embodiment to enhance the echogenic signature of the needle 100. For example, this echogenically enhanced region 128 can be fabricated by, but not limited to, roughening the end of the needle over a predefined length adjacent to at least the first and second tip portions of the distal end 104. The length of the echogenically enhanced region 128 may be in the range of 2 mm to 20 mm, but is more preferably in the range of 10 mm to 15 mm. The echogenic enhanced pattern 128 may be imparted to the needle body 102 via a micro-blasting process which roughens the surface of the needle over a specific length, improving the visibility of the needle under endoscopic ultrasound. In other embodiments, the echogenically enhanced region 128 of the needle 100 may be achieved through the removal of material from the surface of the needle to provide greater reflectivity and strengthened reflected signal. It is contemplated that the removal of material does not, however, reduce the performance of the needle from a pushability perspective or deter its ability to acquire a desired sample.

Figure 14A:
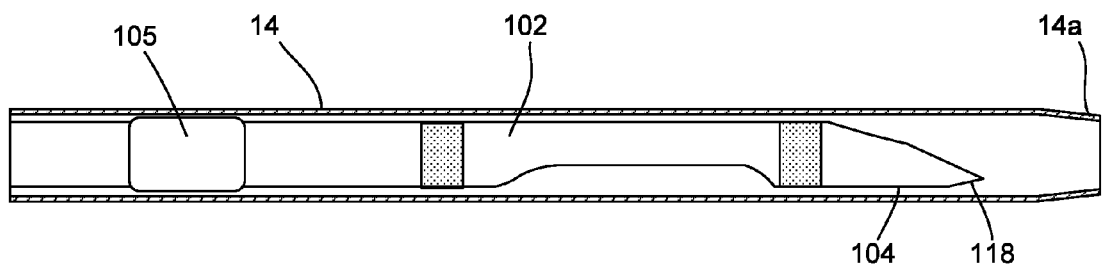
FIG. 14A is a side view, partly in section, of storage of the biopsy needle of FIG. 13 within the sheath of FIG. 1.
Figure 14B:
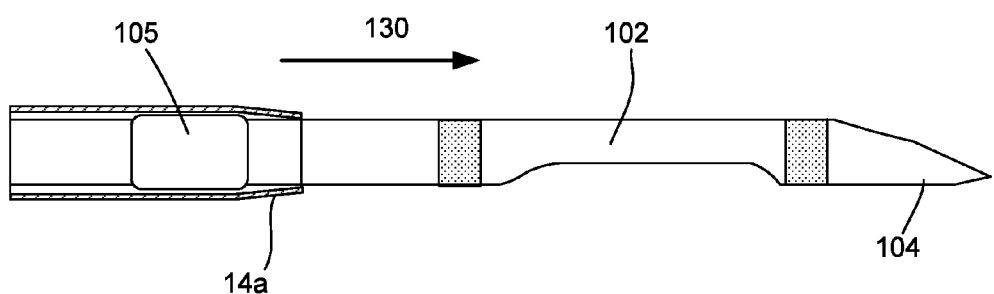
FIG. 14B is a side view, partly in section, of extension of the biopsy needle of FIG. 13 from the sheath of FIG. 1.

FIGS. 14A and 14B are side views, partly in section, of storage and extension of the biopsy needle 100 of FIG. 13 within the sheath 14 of the delivery system of FIG. 1. Referring to FIG. 14A, the needle 100 is shown loaded within the sheath 14 with the device handle in the fully retracted position and ready for extension into a target site for sample collection. In this instance, the distal end 104 of the needle 100 lies proximal to the distal tapered end 14a of the sheath 14. FIG. 14B illustrates the position of the needle 100 and needle collet 105 relative the sheath 14 when the needle transitions to a fully extended position, as indicated by arrow 130. In the fully extended position, the needle collet 105 remains housed inside sheath 14, proximal to the tapered distal tip, thereby preventing the needle 100 from extending past a set distance from the sheath 14.

It is important that the needle 100 can be passed through an internal diameter of a sheath 14 of the delivery device (shown in FIG. 1) without catching on an internal wall of same, particularly during tissue collection procedures and/or needle exchange. As the needle advances, the heel of the back-cut grind 118 may come in contact with the internal diameter of the sheath 14 and reduce the friction between the distal end 104 of the needle 100, particularly the pointed tip 116 and the sheath 14. In this way, the needle 200 can be smoothly tracked through the sheath to exit the end of the sheath. This feature also makes it easy to remove a needle and re-insert a new needle while the rest of a delivery device remains within a patient during a procedure.

Figure 15:
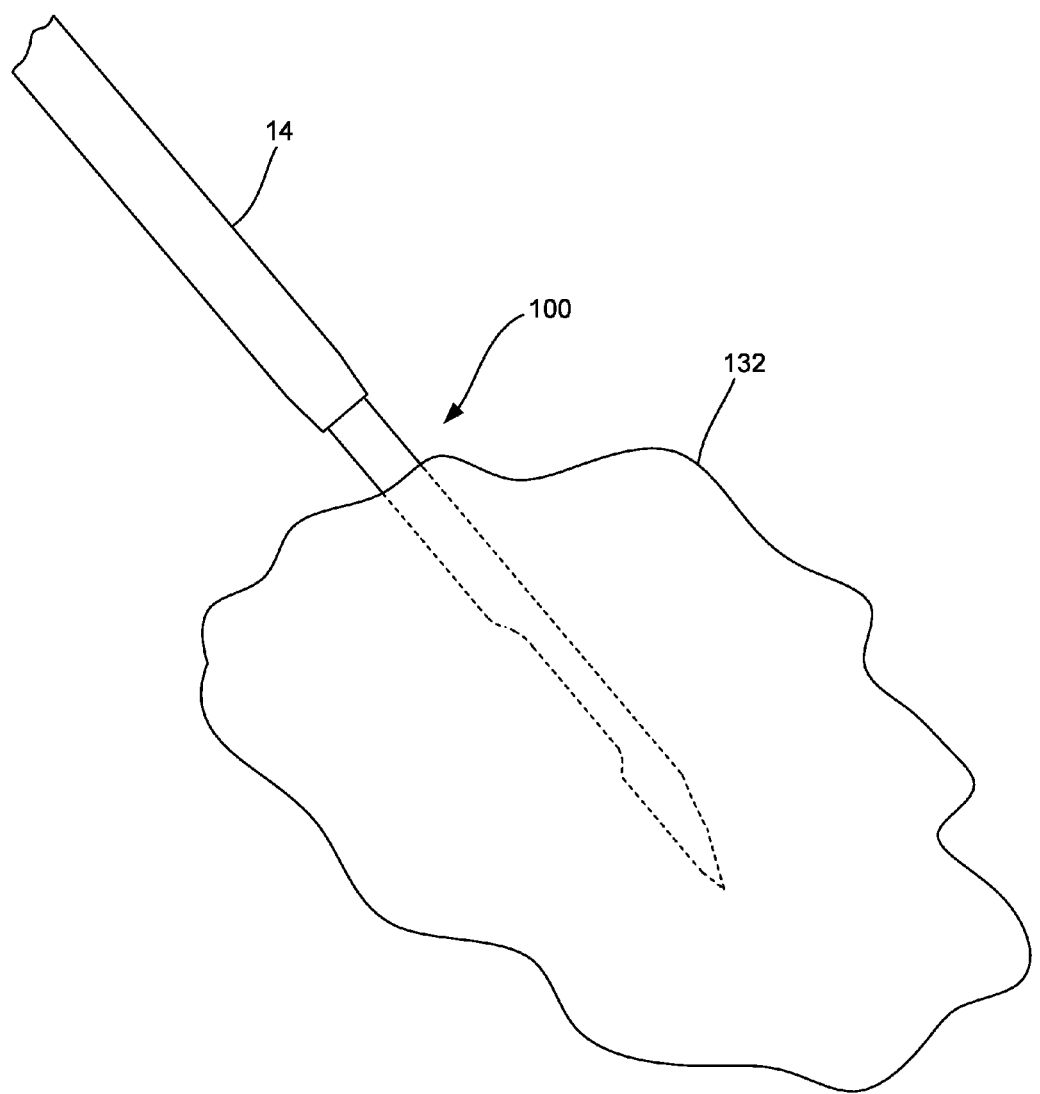
FIG. 15 illustrates the biopsy needle of FIG. 5 inserted into a sample tissue for collection of a portion of the sample tissue.
Figure 16:
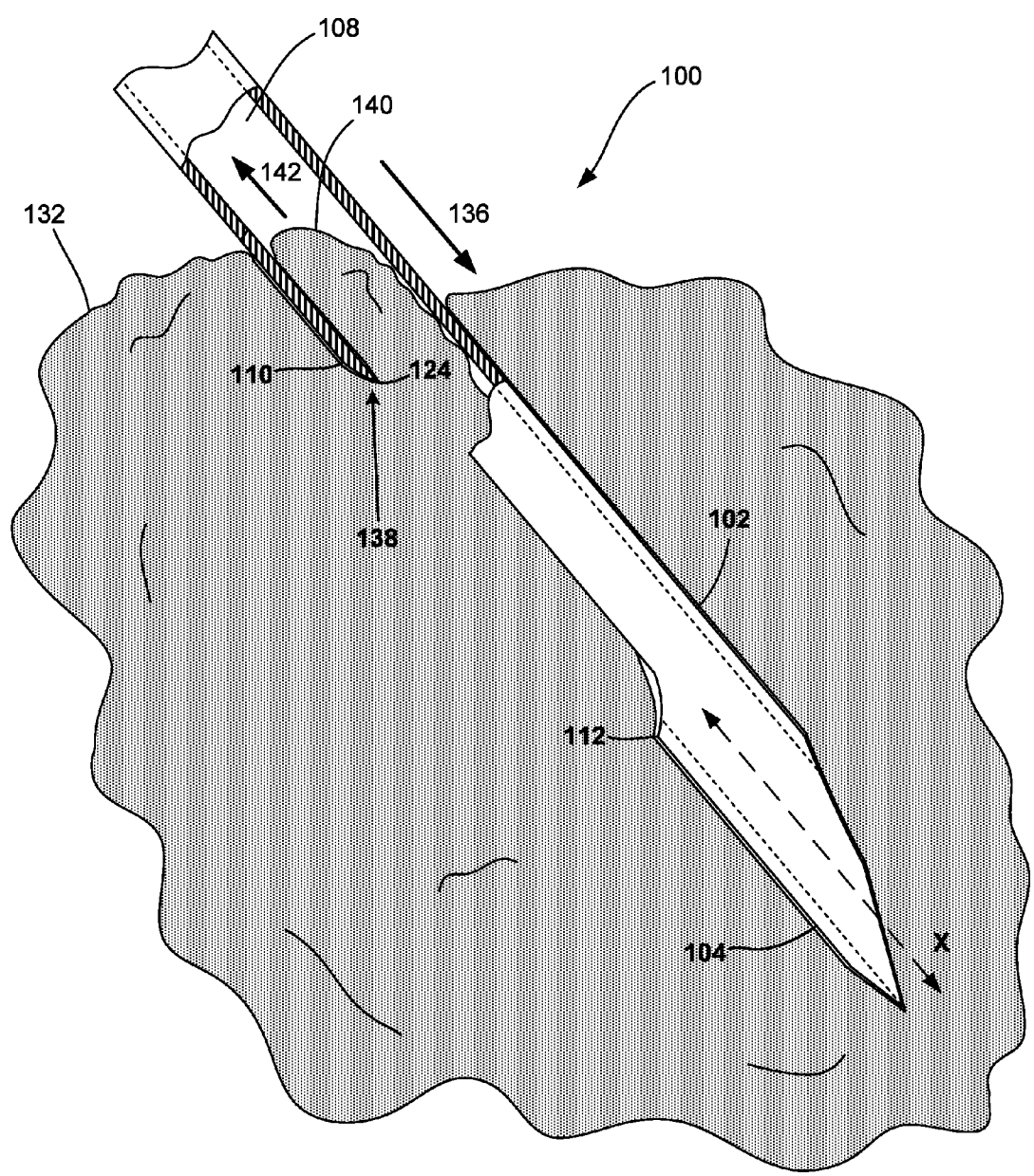
FIG. 16 is an enlarged side view, partly in section, illustrating a sample tissue collection procedure using the biopsy needle of FIG. 5 consistent with the present disclosure.
Figure 17:
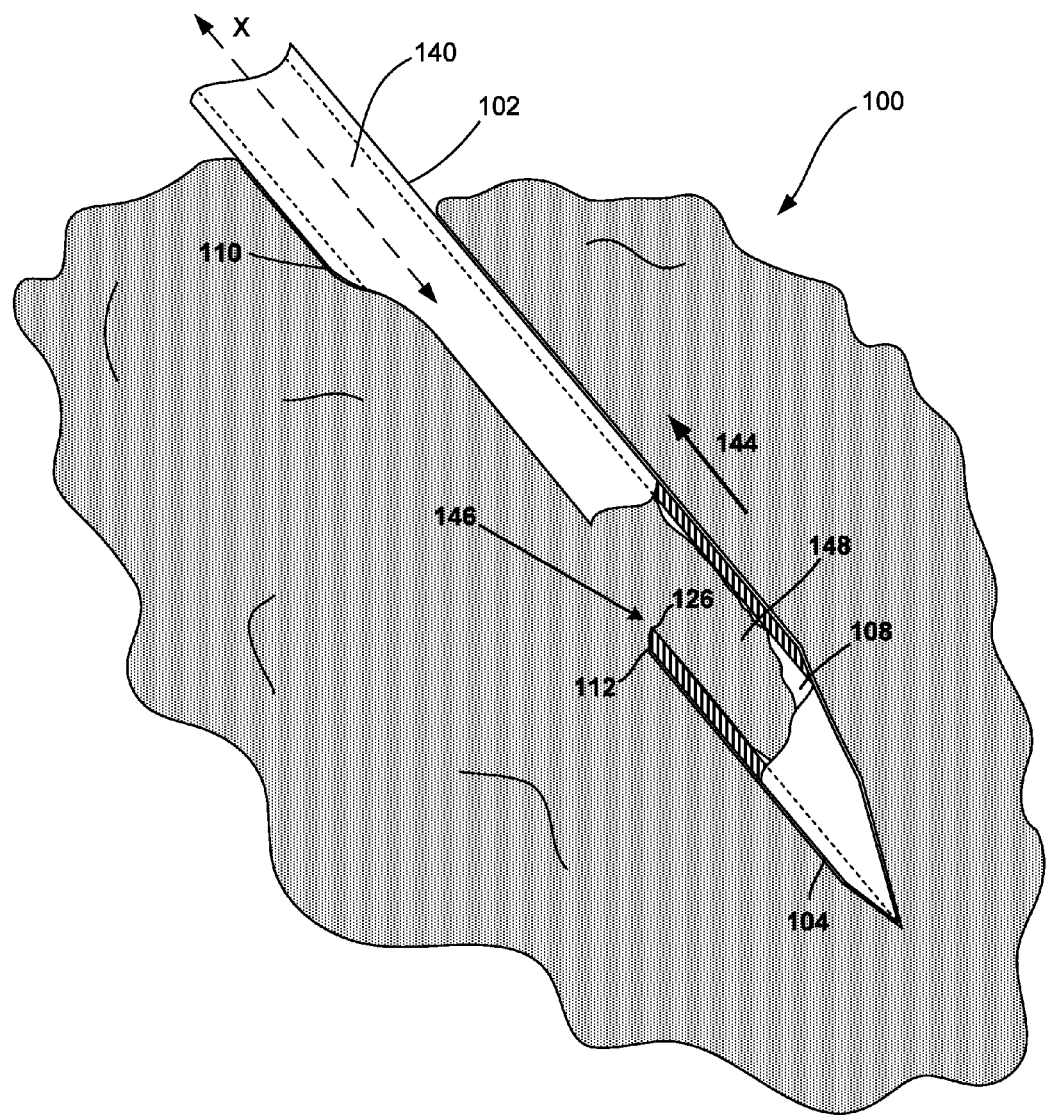
FIG. 17 is an enlarged side view, partly in section, illustrating a sample tissue collection procedure using the biopsy needle of FIG. 5 consistent with the present disclosure.

FIG. 15 illustrates the biopsy needle 100 of FIG. 5 inserted into a sample tissue 132 for collection (e.g., biopsy or harvesting) of at least a portion of the sample tissue 132. FIGS. 16 and 17 are enlarged side views, partly in section, of the distal end 104 and cutting slot 106 inserted within the sample tissue 132, illustrating sample tissue collection procedures using the biopsy needle 100. As shown, the needle 100 may be extended from the sheath 14 when delivered to a target site. An operator (e.g., physician or other trained medical personnel) may then advance the distal end 104 of the needle 100 towards the target tissue 132 to be sampled (with or without the assistance of use of ultrasound techniques). Upon piercing and entering the tissue 132, an operator may then begin the collection of tissue. In the illustrated embodiment, the target tissue 132 may be an abnormal mass, such as a tumor or the like.

As previously described, the proximal cutting end 110 of the cutting slot 106 may include a cutting edge 124. Accordingly, as shown in FIG. 16, upon movement of the needle body 100 in a distal direction along the longitudinal axis X, as indicated by arrow 136, the cutting edge 124 of the proximal cutting end 110 is configured to make contact with the tissue 132, as indicated by arrow 138, and further excise a sample material 140 therefrom and into the lumen 108, as indicated by arrow 142. In one embodiment, a vacuum may be communicated from the proximal end to at least the cutting slot 106 through the lumen 108 so as to provide a suction force to the target tissue 132 and further assist in collection and harvesting of the tissue sample 138 via aspiration.

The distal cutting end 112 of the cutting slot 106 may also, or alternatively, include a cutting edge 126. Accordingly, as shown in FIG. 17, upon movement of the needle body 100 in a proximal direction along the longitudinal axis X, as indicated by arrow 144, the cutting edge 126 of the distal cutting end 112 is configured to make contact with the tissue 132, as indicated by arrow 146, and further excise a sample material 148 therefrom and into the lumen 108. Similarly, a vacuum may be communicated from the proximal end to at least the cutting slot 106 through the lumen 108 so as to provide a suction force to the target tissue 132 and further assist in collection and harvesting of the tissue sample 148 via aspiration.

In some embodiments, at least one of the opposing sidewalls 114a, 114b may include a cutting edge extending along a length thereof, such that the cutting edge is configured to contact and excise a sample material upon rotational movement of the needle body 102 about the longitudinal axis X.

In one embodiment, the collection of tissue may involve multiple passes of the proximal and distal cutting ends 110, 112 within the tissue sample 132. For example, the needle 100 may be moved in a back-and-forth motion for a number of repetitions (e.g., within the range of 1 to 20 repetitions) so as to harvest a representative sample of the tissue.

Figure 18:
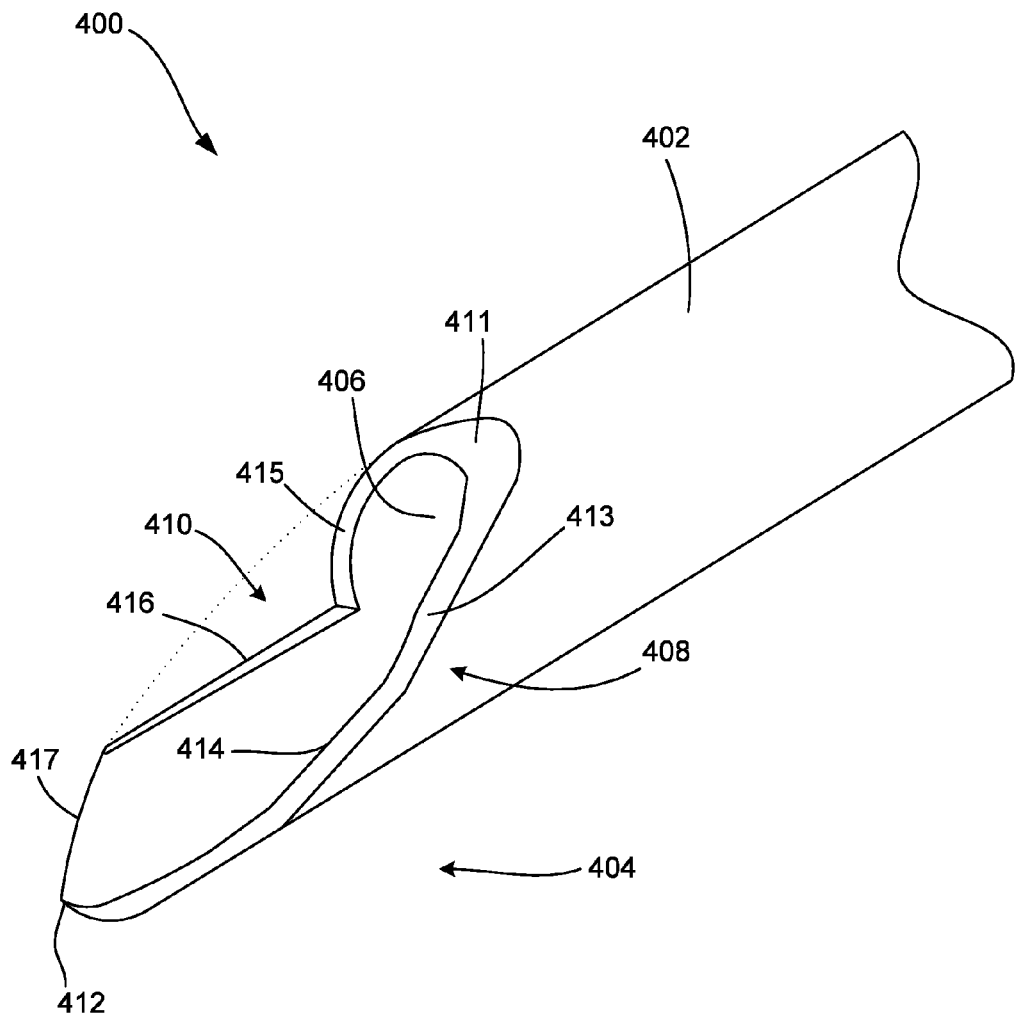
FIG. 18 is a perspective view of a portion of another embodiment of a biopsy needle consistent with the present disclosure.
Figure 19:
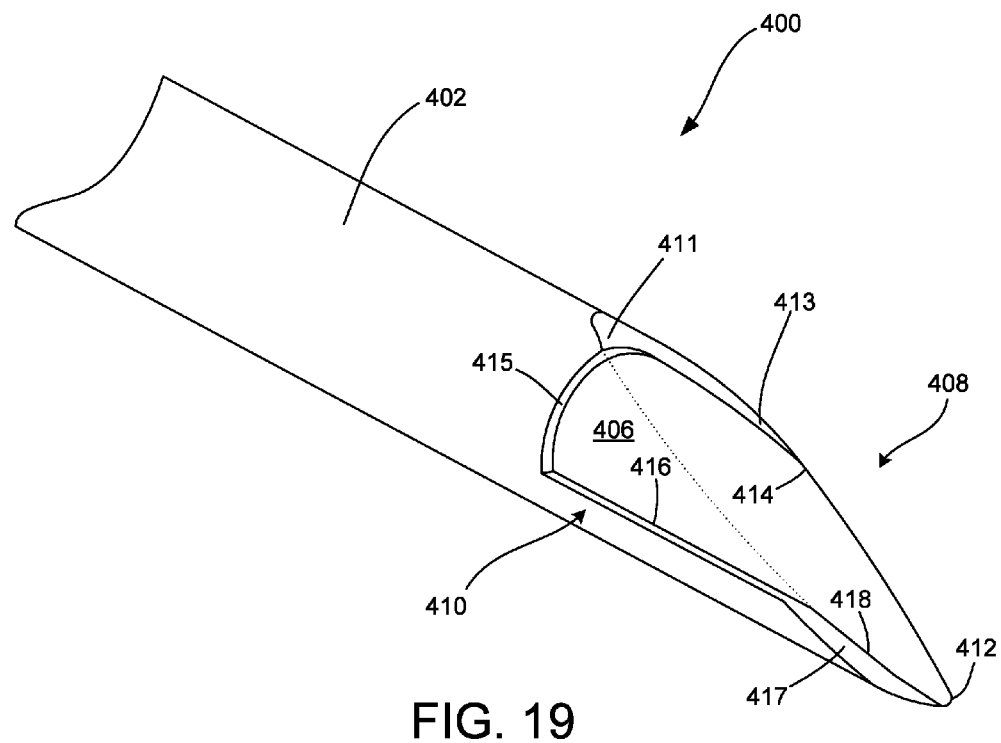
FIG. 19 is a perspective view of a portion of another embodiment of a biopsy needle consistent with the present disclosure.
Figure 20:
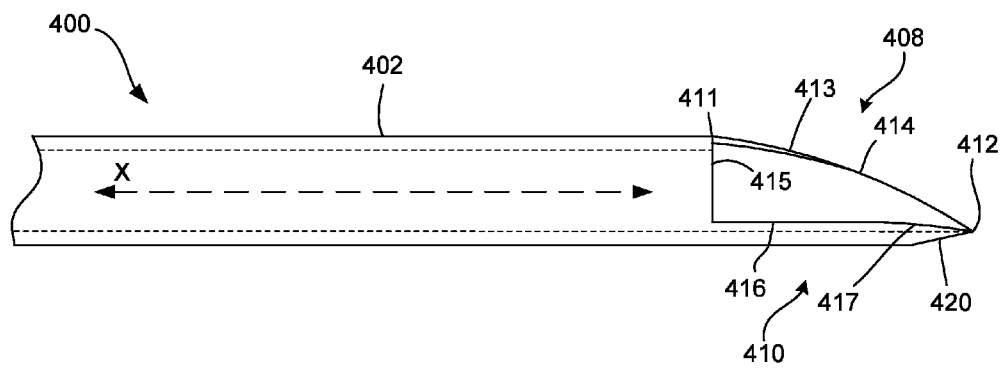
FIG. 20 is a side profile view of the distal end of the biopsy needle of FIGS. 18 and 19.

FIGS. 18 and 19 are perspective views of another embodiment of a biopsy needle 400 consistent with the present disclosure. FIG. 20 is a side profile view of the distal end 404 of the biopsy needle 400 of FIGS. 18 and 19. The biopsy needle 400 generally includes an elongate tubular body 402 having a longitudinal axis X. The body 402 further includes an open proximal end (not shown), an open distal end 404, an outer surface, and an inner surface defining a lumen 406 extending along the longitudinal axis X between the proximal end and distal end 404.

The needle 400 further includes a cutting tip defined on the distal end 404 of the body 402. The cutting tip generally includes a first portion 408 and a second portion 410, each extending from a proximal surface 411 of the cutting tip and converging at a pointed end 412 of the cutting tip. As shown, the first and second portions 408, 410 are generally formed on opposing sides of the needle body 402. The first portion 408 is from at least a first bevel grind 413 that extends from the proximal surface 411 of the cutting tip and terminates at the pointed end 412. The first bevel grind 413 is oblique to the outer surface of the needle body 402. The first portion 408 further includes a curvilinear, or arcuate, cutting edge 414 extending along a length of the first bevel grind 413 between the proximal surface 411 and the pointed end 412 of the cutting tip. During a tissue collection procedure, the cutting edge 414 is configured to excise tissue upon contact therewith. The first portion 408 generally acts a coring element, such that, upon rotational movement of the needle body 402 about the longitudinal axis X, the cutting edge 414 is configured to shear a tissue sample and further draw the sheared tissue into the lumen 406 of the needle body 402 for harvesting, as described in greater detail herein.

The second portion 410 of the cutting tip generally defines a side slot formed from a second set of bevel grinds. The second portion 410 is generally formed by removal of a beveled portion of the needle body 402 opposing the first portion 408 and substantially identical thereto, as generally illustrated by the dotted line in FIG. 18. The second set of bevel grinds includes a second bevel grind 415 extending from the proximal surface 411 and lying along a plane that is oblique to a longitudinal plane along which the needle body 402 lies. More specifically, the second bevel grind 415 is generally orthogonal to the longitudinal axis X of the body 402. The second set of bevel grinds further includes a third bevel grind 416 extending from the second bevel grind 416 and towards the pointed end 412 of the cutting tip. The third bevel grind 416 is substantially parallel to the longitudinal axis X of the body 402. A fourth bevel grind 417 extends from the third bevel grind 416 and terminates at the pointed end 412 of the cutting tip. The fourth bevel 417 is oblique to the third bevel grind 416. In the illustrated embodiment, the first bevel grind 413 and the fourth bevel grind 417 may be the same. At least one of the second, third, and fourth bevel grinds 415, 416, 417 may include a cutting edge along a length thereof to assist in sample collection. For example, at least the fourth bevel grind 417 may include cutting edge 418 configured to excise a sample material (e.g., tissue) upon contact therewith to assist in sample collection during a biopsy procedure. As shown in FIG. 20, the cutting tip may further include a back-cut bevel grind 420 oblique to the outer surface of the body 402 and proximate to and terminating at the pointed end 412 of the cutting tip. The back-cut bevel grind 420 is similar to the back-cut bevel grind 118 of needle 100 and provides the same advantages previously described herein.

It should be noted that biopsy needle 400 is configured to be used with the delivery system of FIG. 1. Accordingly, the biopsy needle 400 may further include additional elements, including, but not limited to, a collet and/or an echogenically enhanced or acoustic reflection region, as shown in FIGS. 13 and 14A-14B with respect to needle 100, and further provide the same benefits associated with each when performing a biopsy procedure.

Figure 21:
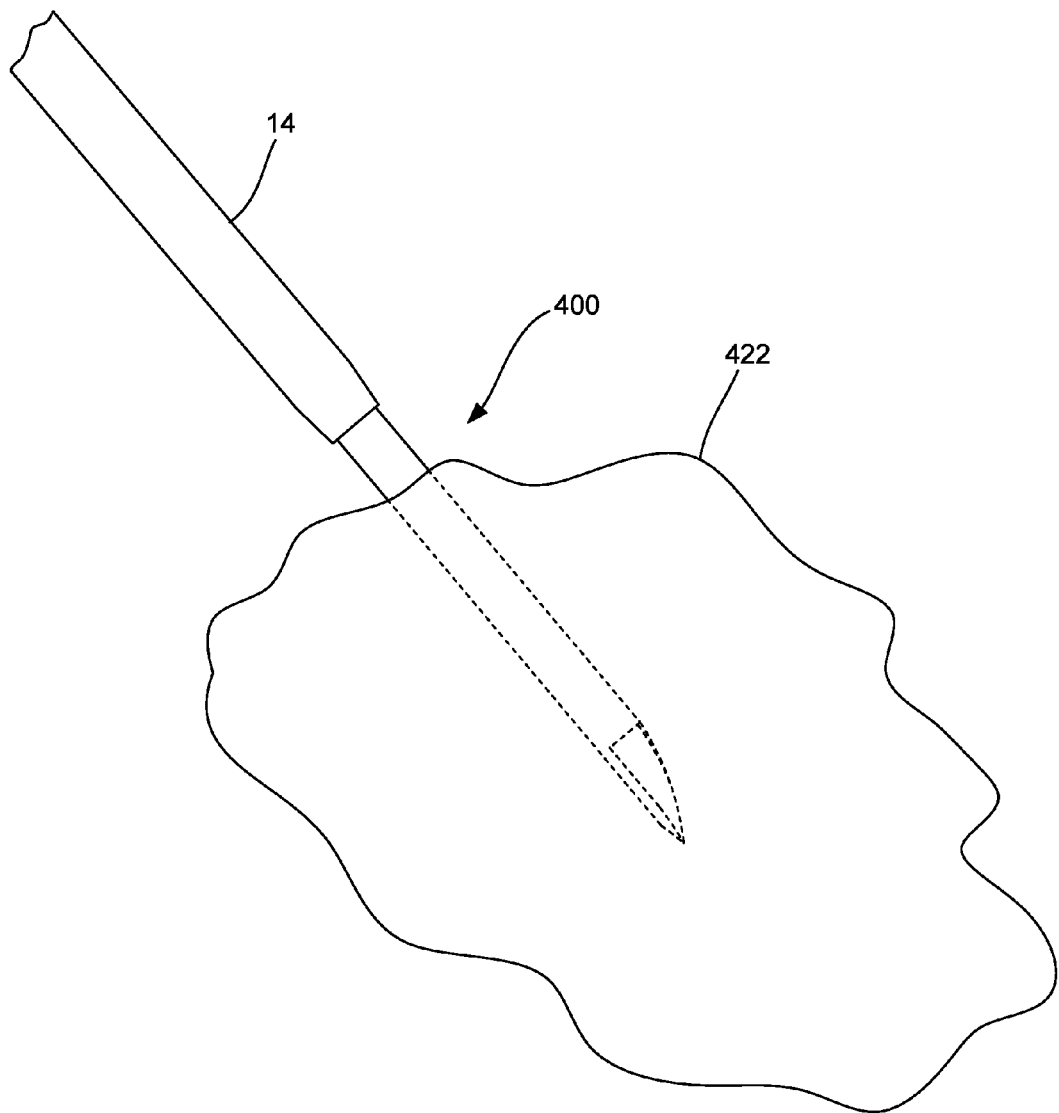
FIG. 21 illustrates the biopsy needle of FIGS. 18-20 inserted into a sample tissue for collection of a portion of the sample tissue.
Figure 22:
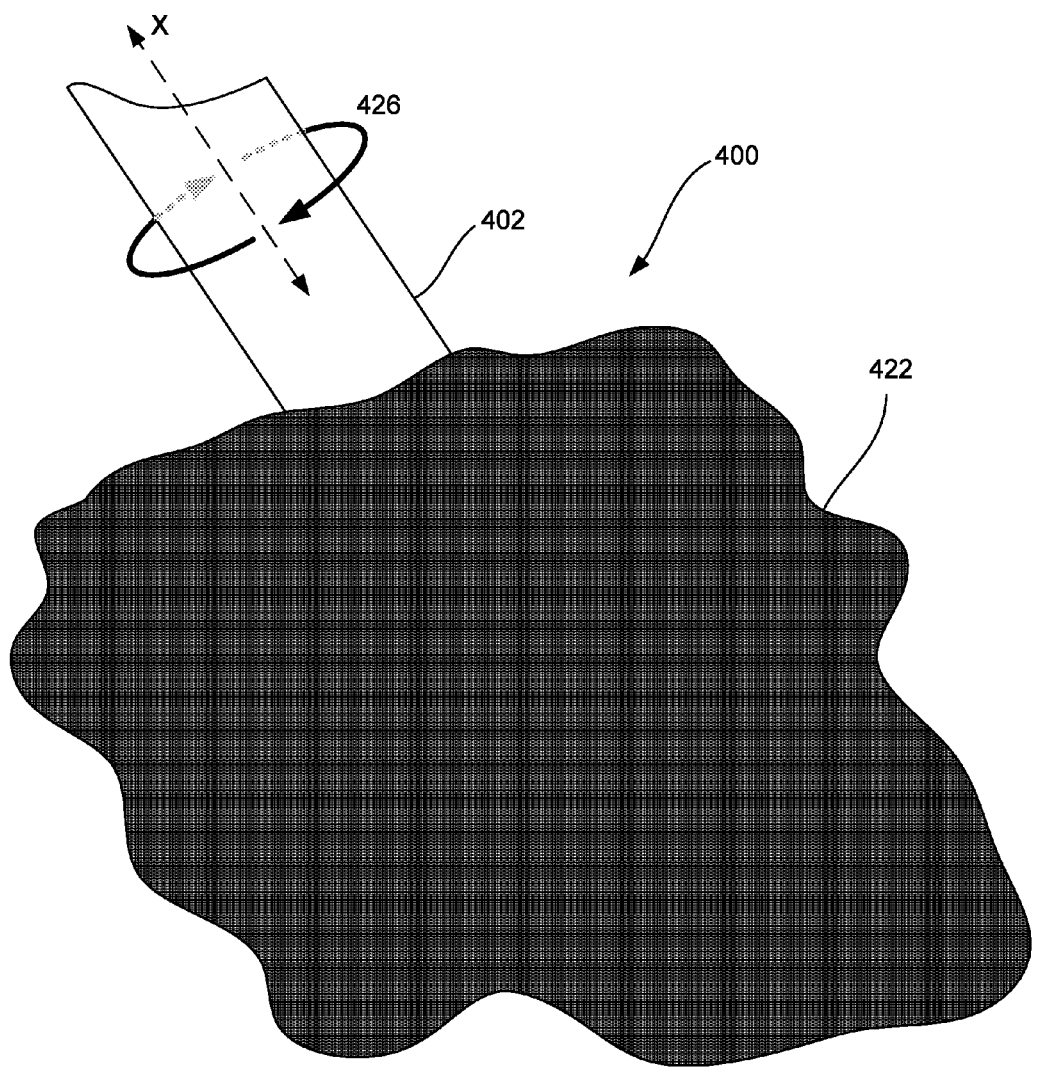
FIG. 22 is an enlarged perspective view illustrating the initiation of sample tissue collection with the biopsy needle of FIGS. 18-20 consistent with the present disclosure.

FIG. 21 illustrates the biopsy needle 400 of FIGS. 18-20 inserted into a sample tissue 422 for collection (e.g., biopsy or harvesting) of at least a portion of the sample tissue 422. FIG. 22 is an enlarged perspective view of the cutting tip of the biopsy needle 400 inserted into the sample tissue 422, illustrating the initiation of sample tissue collection with the biopsy needle 400. As shown, the needle 400 may be extended (from the sheath 14 of the delivery system of FIG. 1) when delivered to a target site. An operator (e.g., physician or other trained medical personnel) may then advance the distal end 404 of the needle 400 towards the target tissue 422 to be sampled (with or without the assistance of use of ultrasound techniques). Upon piercing and entering the tissue 422, an operator may then begin the collection of tissue. In the illustrated embodiment, the target tissue 420 may be abnormal mass, such as a tumor or the like, for example.

Upon movement of the needle body 402 in a distal direction along the longitudinal axis X, as indicated by arrow 424, the pointed end 412 of the cutting tip is configured to make contact with and pierce the tissue 422. Upon entering and residing within the tissue 422, at least cutting edge 418 formed on the second portion 410 of the cutting tip may excise a portion of the tissue 422 and allow a sample of tissue to be collected within the lumen 406. The operator may then rotate the needle 400 about the longitudinal axis X, as indicated by arrow 426. In particular, the operator may rotate the needle hub 17 of the delivery system while the needle 400 is extended from the sheath 14 and within the tissue 422. For example, in one embodiment, the needle hub 17 of the needle sub-assembly 15 (shown in FIGS. 2 and 4) may be configured to rotate while releasably coupled to the handle 10 of the delivery device by way of the thumb latch 28. Upon rotating the needle hub 17, the distal end 404 of the needle 400 may rotate about the longitudinal axis X in a direction resulting in the cutting edge 414 of the first portion 408 to excise and effectively shear a core tissue sample from the tissue 422. In one embodiment, a vacuum may be communicated from the proximal end of the needle body 402 to the distal end 404 of the needle body 402 through the lumen 406 so as to provide a suction force to the target tissue 422 and further assist in collection and harvesting of the tissue sample via aspiration during the coring technique.

The distinct configuration of the cutting tip of the needle 400 provides improved tissue collection. In particular, the use of a coring technique, by way of rotational movement, in conjunction with the conventional lateral movement ensures that the needle is guided into the tissue in a controlled manner, thereby minimizing the opportunity for needle mishits or needle shaft deflection when attempting to collect a sample. Additionally, the coring element of the cutting tip further allows tissue to be guided into the lumen in controlled manner and further maximizes the amount of tissue to be harvested.

Figure 23:
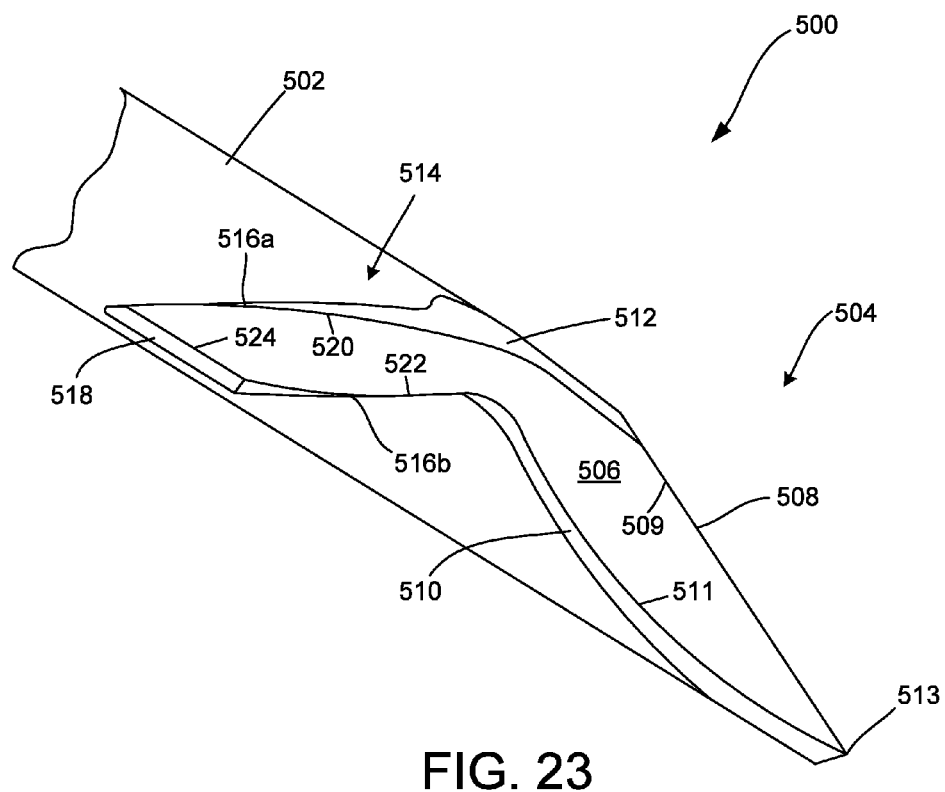
FIG. 23 is a perspective view of a portion of another embodiment of a biopsy needle consistent with the present disclosure.
Figure 24:
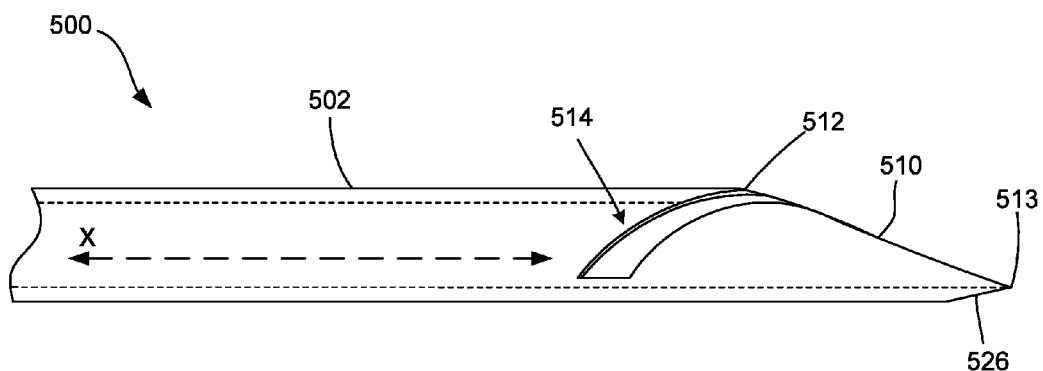
FIG. 24 is a side profile view of the distal end of the biopsy needle of FIG. 23.

FIG. 23 is a perspective view of a portion of another embodiment of a biopsy needle 500 consistent with the present disclosure. FIG. 24 is a side profile view of the distal end 504 of the biopsy needle 500 of FIG. 23. The biopsy needle 500 generally includes an elongate tubular body 502 having a longitudinal axis X. The body 502 further includes an open proximal end (not shown), an open distal end 504, an outer surface, and an inner surface defining a lumen 506 extending along the longitudinal axis X between the proximal end and distal end 504.

The open distal end 504 is formed from at least first and a second angular bevel grinds 508, 510, oblique to the outer surface of the needle body 502. Each of the first and second bevel grinds 508, 510 generally extend from a proximal surface 512 of the distal end 504 and terminate at a pointed tip 513. At least one of the first and second bevel grinds 508, 510 may define a cutting edge configured for excising a sample material when in contact therewith, particularly during a biopsy procedure. In the illustrated embodiment, each of the first and second bevel grinds 508, 510 defines a cutting edge 509, 511, respectively.

The biopsy needle 500 further includes a cutting slot 514 extending from the open distal end in a direction away from the pointed tip 513 and towards the proximal portion of the needle body 502. The cutting slot 514 extends through the outer and inner surfaces and into the lumen 506 of the body 502. The cutting slot 514 includes opposing sidewalls 516*a*, 516*b* extending from the proximal surface 512 of the open distal cutting end 504 and terminating at a base wall 518. As shown, the opposing sidewalls 516*a*, 516*b* are formed from third and fourth distinct angular bevel grinds extending from the proximal surface 512 of the open distal cutting end 504, generally in a diagonal direction relative to a longitudinal plane along which the needle body 402 lies. The base wall 518 is formed from a fifth bevel grind oblique to the third and fourth bevel grinds. As shown, the fifth bevel grind may be substantially parallel to the longitudinal axis X of the needle body 502. In one embodiment, the cutting slot 514 generally has a helical shape, such that the sidewalls 516*a*, 516*b* revolve about the outer surface of the body 502 relative to the longitudinal axis X. Depending on the type of sample to be collected, as well as the target site from which the sample is to be collected, the cutting slot 514 may extend between 0.1 to 0.9 revolutions about the needle body 502 (as measured between the proximal surface 512 of the distal end 504 to the base wall 518 of the cutting slot 514 about the longitudinal axis X along the circumference of the needle body 502). In one embodiment, the helical cutting slot extends approximately 0.35 revolutions along the needle body 502.

At least one of the opposing sidewalls 516*a*, 516*b* and base wall 518 may define a cutting edge configured for excising a sample material when in contact therewith, particularly during a biopsy procedure. For example, each of the opposing sidewalls 516*a*, 516*b* may define a corresponding cutting edge 520, 522 and the base wall 518 may also define a cutting edge 524. In the illustrated embodiment, each of the opposing sidewalls 516*a*, 516*b* extends from the first and second bevel grinds 508, 510, respectively, at the proximal surface 512. Accordingly, each of the opposing sidewalls 516*a*, 516*b* may share a corresponding cutting edge with the associate first and second bevel grinds 508, 510, respectively. For example, cutting edge 509 may extend from the pointed tip 513, along the first bevel grind 508 of the distal cutting end 504, along the sidewall 516*a* and terminating at the base wall 518. Similarly, cutting edge 511 may extend from the pointed tip 513, along the second bevel grind 510 of the distal cutting end 504, along the sidewall 516*b* and terminating at the base wall 518.

As shown in FIG. 24, the distal cutting end 504 of the needle 500 may further include back-cut bevel grind 526 oblique to the outer surface of the body 502 and proximate to and terminating at the pointed tip 513. The back-cut bevel grind 526 is similar to the back-cut bevel grind 118 of needle 100 and provides the same advantages previously described herein.

It should be noted that biopsy needle 500 is configured to be used with the delivery system of FIG. 1. Accordingly, the biopsy needle 500 may further include additional elements, including, but not limited to, a collet and/or an echogenically enhanced or acoustic reflection region, as shown in FIGS. 13 and 14A-14B with respect to needle 100, and further provide the same benefits associated with each when performing a biopsy procedure.

Figure 25:
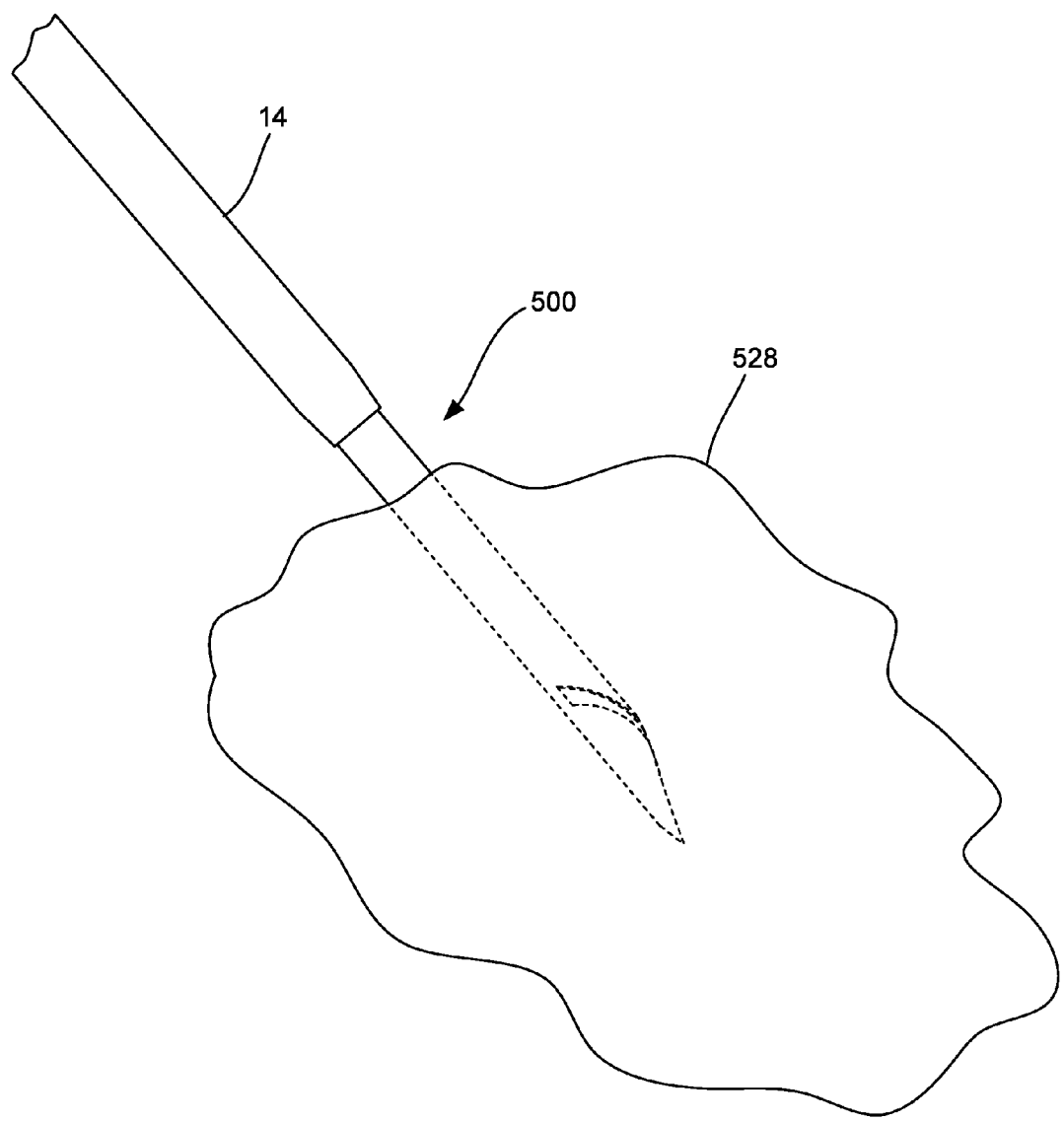
FIG. 25 illustrates the biopsy needle of FIGS. 23-24 inserted into a sample tissue for collection of a portion of the sample tissue.
Figure 26:
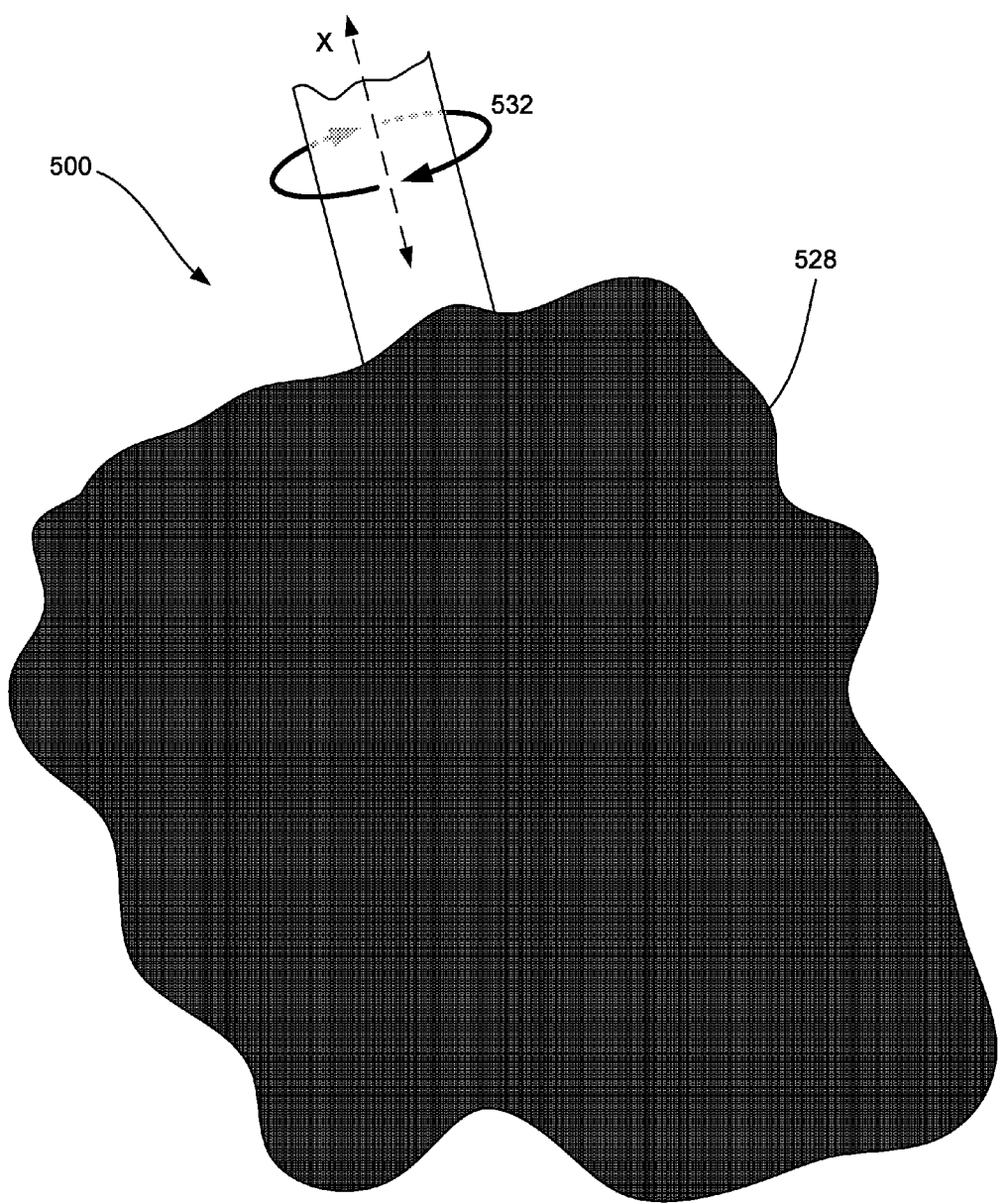
FIG. 26 is an enlarged perspective view illustrating the initiation of sample tissue collection with the biopsy needle of FIGS. 23-24 consistent with the present disclosure.

FIG. 25 illustrates the biopsy needle 500 of FIGS. 23 and 24 inserted into a sample tissue 528 for collection (e.g., biopsy or harvesting) of at least a portion of the sample tissue 528. FIG. 26 is an enlarged perspective view of the distal end 504 and cutting slot 514 inserted within the sample tissue 528, illustrating the initiation of sample tissue collection with the biopsy needle 500. As shown, the needle 500 may be extended (from the sheath 14 of the delivery system of FIG. 1) when delivered to a target site. An operator (e.g., physician or other trained medical personnel) may then advance the distal end 504 of the needle 500 towards the target tissue 528 to be sampled (with or without the assistance of use of ultrasound techniques). Upon piercing and entering the tissue 528, an operator may then begin the collection of tissue. In the illustrated embodiment, the target tissue 528 may be abnormal mass, such as a tumor or the like, for example.

Upon movement of the needle body 502 in a distal direction along the longitudinal axis X, as indicated by arrow 530, the pointed tip 513 of the distal cutting end 504 is configured to make contact with and pierce the tissue 528. Upon entering and residing within the tissue 528, the cutting edges 509, 511 of the first and second bevel grinds 508, 510 may excise portions of the tissue 528 and allow a sample of tissue to be collected within the lumen 506.

Upon forcing the distal cutting end 504 deeper into the targeted tissue 528, the helical cutting slot 514 is configured to further assist is sample tissue collection and drawing a sampled tissue core within the lumen 506. For example, in one embodiment, an operator need only move the needle body 502 in a linear motion in proximal and distal directions, such that as the distal cutting end 504 is forced further into the tissue 528, the cutting edges 520, 522 of the sidewalls 516a, 516b are configured to catch and excise surrounding tissue, thereby effectively shearing a core tissue sample from the tissue 528. Additionally, or alternatively, an operator may rotate the needle 500 about the longitudinal axis X, as indicated by arrow 532, once the distal cutting end 504 has pierced the tissue 528 and the cutting slot 514 is positioned within the tissue 528. In particular, the operator may rotate the needle hub 17 of the delivery system while the needle 500 is extended from the sheath 14 and penetrating the tissue 528. For example, in one embodiment, the needle hub 17 of the needle sub-assembly 15 (shown in FIGS. 2 and 4) may be configured to rotate while releasably coupled to the handle 10 of the delivery device by way of the thumb latch 28. Upon rotating the needle hub 17, the distal end 504, and cutting slot 514, of the needle 500 may rotate about the longitudinal axis X in a direction resulting in the cutting edges 520, 522, and 524 of the opposing sidewalls 516a, 516b, and base wall 518 contacting and excising surrounding tissue. The helical configuration of the cutting slot 514 may draw the tissue in a proximal direction, thereby drawing the sampled tissue into the lumen 506 and effectively shearing a core tissue sample from the tissue 528. In one embodiment, a vacuum may be communicated from the proximal end of the needle body 502 to the distal end 504 of the needle body 502 through the lumen 506 so as to provide a suction force to the target tissue 528 and further assist in collection and harvesting of the tissue sample via aspiration during the helical shearing technique.

The distinct configuration of the cutting tip of the needle 500 provides improved tissue collection. In particular, the helical cutting slot further increases the cutting surface of the distal cutting end, thereby maximizing the amount of tissue that can be harvested. Additionally, the helical cutting slot feature further ensures that the needle is guided into the tissue in a controlled manner, thereby minimizing the opportunity for needle mishits or needle shaft deflection when attempting to collect a sample.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A biopsy needle comprising:
   an elongate tubular body having a longitudinal axis and comprising an open proximal end, an open distal end, an outer surface, and an inner surface defining a lumen extending along the longitudinal axis between the proximal and distal ends; and
   a cutting tip defined on the distal end of the body, the cutting tip comprising first and second portions formed on opposing sides of the needle body and converging at a pointed end of the cutting tip:
   the first portion comprising a coring element formed from a first set of bevel grinds, wherein the first set of bevel grinds comprises a first bevel grind oblique to the longitudinal axis and extending from a proximal surface of the cutting tip and terminating at the pointed end of the cutting tip, wherein the coring element defines a cutting edge configured to excise sample material upon rotational movement of the needle body about the longitudinal axis so as to capture and draw a core of sample material within the lumen of the body; and
   the second portion comprising a side slot formed from a second set of bevel grinds, wherein the second set of bevel grinds opposite the first set of bevel grinds comprises a second bevel grind, a third bevel grind, and a fourth bevel grind, wherein the second bevel grind is orthogonal to the longitudinal axis and extends from the proximal surface of the cutting tip towards the third bevel grind, wherein the third bevel grind is parallel to the longitudinal axis and extends from the second bevel grind towards the pointed end of the cutting tip, and wherein the fourth bevel grind is oblique to the longitudinal axis and extends from the third bevel grind and terminates at the pointed end of the cutting tip.

2. The biopsy needle of claim 1, wherein the first and fourth bevel grinds comprise identical angles.

3. The biopsy needle of claim 1, wherein the cutting tip further comprises a back-cut bevel grind oblique to the outer surface of the body and proximate to the pointed end of the cutting tip for providing a smooth needle passage during needle insertion and withdrawal during a biopsy procedure.

4. The biopsy needle of claim 1, wherein the cutting edge of the coring element extends along a length of the first bevel grind.

5. The biopsy needle of claim 4, wherein the cutting edge extends along the entire length of the first bevel grind from the proximal surface of the cutting tip to the pointed end of the cutting tip.

6. The biopsy needle of claim 1, wherein the lumen is configured to communicate a vacuum from the proximal end to the distal end of the body to provide a suction force to the material to be sampled.

7. The biopsy needle of claim 1, further comprising a section of body adjacent the distal end having enhanced echogenicity or acoustic reflection.

8. The biopsy needle of claim 1, further comprising a collet surrounding a portion of the body and having a diameter sufficient to prevent the needle body from entirely passing through a distal end of a sheath of a biopsy device.

9. The biopsy needle of claim 1, wherein the needle body has an outer diameter in the range of 10-gauge to 30-gauge.

10. The biopsy needle of claim 1, wherein the needle is comprised of a material selected from the group consisting of nitinol, cobalt chrome, stainless steel, a metal alloy, one or more polymers, nanotube composite, and combinations thereof.

* * * * *